(12) United States Patent
Franklin

(10) Patent No.: US 10,973,869 B2
(45) Date of Patent: Apr. 13, 2021

(54) METHODS OF TREATING CARDIOMYOPATHY ASSOCIATED WITH GENETIC DISORDERS

(71) Applicant: CONSTANT THERAPEUTICS LLC, Cambridge, MA (US)

(72) Inventor: Richard Franklin, Cambridge, MA (US)

(73) Assignee: Constant Therapeutics LLC, Cambridge, MA (US)

( * ) Notice: Subject to any disclaimer, the term of this patent is extended or adjusted under 35 U.S.C. 154(b) by 0 days.

(21) Appl. No.: 15/981,310

(22) Filed: May 16, 2018

(65) Prior Publication Data

US 2019/0117726 A1    Apr. 25, 2019

Related U.S. Application Data

(60) Provisional application No. 62/507,607, filed on May 17, 2017.

(51) Int. Cl.
*A61K 38/08* (2019.01)
*A61P 9/06* (2006.01)

(52) U.S. Cl.
CPC .............. *A61K 38/085* (2013.01); *A61P 9/06* (2018.01)

(58) Field of Classification Search
None
See application file for complete search history.

(56) References Cited

FOREIGN PATENT DOCUMENTS

WO  WO2014/021942   2/2014
WO  WO2014/189634   11/2014

OTHER PUBLICATIONS

Sabharwal et al. ("Angiotensin-Dependent Autonomic Dysregulation Precedes Dilated Cardiomyopathy in a Mouse Model of Muscular Dystrophy," Exp Physiol. Jul. 1, 2015; 100(7): 776-795) (Year: 2015).*
Quinlan et al. ("Evolution of the mdx mouse cardiomyopathy: physiologicaland morphological findings," Neuromuscular Disorders 14 (2004) 491-496) (Year: 2004).*
Beynon et al. ("Cardiac involvement in muscular dystrophies," Q J Med 2008; 101:337-344) (Year: 2008).*
Verhaert et al. ("Cardiac Involvement in Patients with Muscular Dystrophies: Magnetic Resonance Imaging Phenotype and Genotypic Considerations," Circ Cardiovasc Imaging. Jan. 2011 ; 4(1): 67-76) (Year: 2011).*
Sabharwal, R. et al., "Angiotensin-(1-7) Delays Onset of Dilated Cardiomyopathy in Mice with Muscular Dystrophy", vol. 30, No. 1 Supplement, The FASEB Journal, Abstract, Published Online: Apr. 1, 2016, Abstract No. 754.7, https://www.fasebj.org/doi/10.1096/fasebj.30.1_supplement.754.7, (1 page).

* cited by examiner

*Primary Examiner* — Christina Bradley
(74) *Attorney, Agent, or Firm* — Proskauer Rose LLP; Fangli Chen; Julio J. Mendez

(57) ABSTRACT

The present invention provides, among other things, methods of treating a cardiac disease or condition in a patient having muscular dystrophy that can include administering to a subject suffering from, susceptible, or diagnosed with muscular dystrophy an angiotensin (1-7) peptide.

19 Claims, No Drawings

Specification includes a Sequence Listing.

METHODS OF TREATING CARDIOMYOPATHY ASSOCIATED WITH GENETIC DISORDERS

CROSS-REFERENCE TO RELATED APPLICATIONS

This application claims the benefit of U.S. Provisional Patent Application Ser. No. 62/507,607 filed May 17, 2017, the contents of which are hereby incorporated herein by reference in their entirety for all purposes.

INCORPORATION BY REFERENCE OF SEQUENCE LISTING

The instant application contains a Sequence Listing which has been filed electronically in ASCII format and is hereby incorporated by reference in its entirety. Said ASCII copy, created on Jan. 3, 2019, is named TXP-025US_SL.txt and is 2,576 bytes in size.

FIELD

The present invention relates to generally to the treatment of cardiac disease or disorder in patients with muscular dystrophy.

BACKGROUND

Muscular Dystrophy (MD) refers to a group of diseases in which muscle fibers are abnormally susceptible to damage. Some subtypes, like Duchenne muscular dystrophy (DMD), typically manifest very early in life. Current treatments for muscular dystrophy include corticosteroid administration, use of orthopaedic devices to support locomotion and prevent contractures, and physiotherapy. Unfortunately, none of the currently used treatments have proven capable of arresting or reversing the progression of the disease.

SUMMARY

Cardiac dysfunction occurs in most muscular dystrophy patients in the course of the disease and cardiac failure. Cardiac function in muscular dystrophy patients does not improve on standard cardiac therapy. Thus, the present invention provides a new therapy for muscular dystrophy patients with cardiac dysfunction and can result in improved cardiac function in muscular dystrophy, rather than just stabilization.

It is understood that any of the aspects and embodiments described below can be combined in any desired way, and that any embodiment or combination of embodiments can be applied to each of the aspects described below, unless the context indicates otherwise.

In one aspect, the invention provides a method of treating cardiac disease or disorder in a patient diagnosed with muscular dystrophy, the method comprising administering an angiotensin (1-7) peptide to the patient.

In some embodiments, the patient is non-ambulatory.

In some embodiments, the muscular dystrophy is Duchenne muscular dystrophy (DMD or Becker muscular dystrophy.

In some embodiments, the cardiac disease or disorder is cardiomyopathy.

In some embodiments, the cardiomyopathy is genetic.

In some embodiments, the genetic cardiomyopathy is hypertrophic cardiomyopathy (HCM), arrhythmogenic right ventricular cardiomyopathy/dysplasia (ARVC/D), conduction system diseases, LV non-compaction, an ion channelopathy, long-QT syndrome (LQTS), Brugada syndrome, catecholaminergic polymorphic ventricular tachycardia (CPVT), short-QT syndrome (SQTS) or idiopathic ventricular fibrillation.

In some embodiments, the cardiac disease or disorder is cardiac arrhythmia.

In some embodiments, the cardiac arrhythmia is sinus tachycardia.

In some embodiments, the cardiac disease or disorder is LVD.

In some embodiments, the LVD is low left ventricular ejection fraction.

In some embodiments, the angiotensin (1-7) peptide is a peptide of SEQ ID NO:1.

In some embodiments, the angiotensin (1-7) peptide is a functional equivalent of SEQ ID NO:1.

In some embodiments, the angiotensin (1-7) peptide is administered in an amount of about 0.1 mg/kg to about 5.0 mg/kg.

In some embodiments, the angiotensin (1-7) peptide is administered in an amount of about 0.5 mg/kg to about 2.0 mg/kg.

In some embodiments, the administration is in an amount that is about 0.5 mg/kg, about 0.6 mg/kg, about 0.7 mg/kg, about 0.8 mg/kg, about 0.9 mg/kg, about 1.0 mg/kg, about 1.1 mg/kg, about 1.2 mg/kg, about 1.3 mg/kg, about 1.4 mg/kg, or about 1.5 mg/kg of the angiotensin (1-7) peptide.

In some embodiments, the angiotensin (1-7) peptide is administered in an amount of 1.0 mg/kg.

In some embodiments, the angiotensin (1-7) peptide is administered subcutaneously.

In some embodiments, the angiotensin (1-7) peptide is administered once daily.

In some embodiments, the angiotensin (1-7) peptide is administered for a period of about one to about twenty-four months.

In some embodiments, the angiotensin (1-7) peptide is administered for about one month, about two months, about three months, about four months, about five months, about six months, about seven months, about eight months, about nine months, about ten months, about eleven months, or about twelve months.

In some embodiments, the method further comprises administering a second therapeutic agent for treating the cardiac disease or disorder.

In some embodiments, the patient has a substantially stable cardiac function.

In some embodiments, the patient has been prescribed medication for the cardiac disease or disorder.

In another aspect, the invention provides a method of treating a cardiac disease or disorder in a patient in need thereof comprising subcutaneously administering a pharmaceutical composition once-daily to a non-ambulatory patient diagnosed with Duchenne muscular dystrophy (DMD) or Becker muscular dystrophy, wherein the pharmaceutical composition comprises: an angiotensin (1-7) peptide in an amount that results in a dosage of about 0.1 mg/kg to about 5.0 mg/kg of the angiotensin (1-7) peptide to the patient, and a pharmaceutically acceptable excipient, and wherein the once-daily administration occurs for a period that is about one to about twenty-four months.

In some embodiments, the pharmaceutical composition comprises an angiotensin (1-7) peptide in an amount that results in a dosage of about 0.5 mg/kg to about 2.0 mg/kg of the angiotensin (1-7) peptide.

In some embodiments, the pharmaceutical composition comprises an angiotensin (1-7) peptide in an amount that results in a dosage of about 0.5 mg/kg, about 0.6 mg/kg, about 0.7 mg/kg, about 0.8 mg/kg, about 0.9 mg/kg, about 1.0 mg/kg, about 1.1 mg/kg, about 1.2 mg/kg, about 1.3 mg/kg, about 1.4 mg/kg, or about 1.5 mg/kg of the angiotensin (1-7) peptide.

In some embodiments, wherein the angiotensin (1-7) peptide is a peptide of SEQ ID NO:1.

In some embodiments, the angiotensin (1-7) peptide is a functional equivalent of SEQ ID NO:1.

In some embodiments, the administration is for at least about one month, about two months, about three months, about four months, about five months, about six months, about seven months, about eight months, about nine months, about ten months, about eleven months, or about twelve months.

In some embodiments, the cardiac disease or disorder is cardiomyopathy, cardiac arrhythmia, heart failure, left ventricular dysfunction (LVD), myocardial fibrosis (MF), or a conduction disorder.

In some embodiments, the cardiac disease or disorder is cardiomyopathy.

In some embodiments, the cardiomyopathy is genetic.

In some embodiments, the genetic cardiomyopathy is hypertrophic cardiomyopathy (HCM), arrhythmogenic right ventricular cardiomyopathy/dysplasia (ARVC/D), conduction system diseases, LV non-compaction, an ion channelopathy, long-QT syndrome (LQTS), Brugada syndrome, catecholaminergic polymorphic ventricular tachycardia (CPVT), short-QT syndrome (SQTS) or idiopathic ventricular fibrillation.

In some embodiments, the cardiac disease or disorder is cardiac arrhythmia.

In some embodiments, the cardiac arrhythmia is sinus tachycardia.

In some embodiments, the cardiac disease or disorder is LVD.

In some embodiments, the LVD is low left ventricular ejection fraction.

In another aspect, the invention provides a unit dosage form for subcutaneous administration, the unit dosage form comprising an effective amount of an angiotensin (1-7) peptide and a pharmaceutically acceptable excipient, wherein the unit dosage form is suitable for the administration of about 0.1 mg/kg to about 5.0 mg/kg of the angiotensin (1-7) peptide.

In some embodiments, the unit dosage form comprises an amount of an angiotensin (1-7) peptide suitable for the administration of about 0.5 mg/kg to about 2.0 mg/kg of the angiotensin (1-7) peptide.

In some embodiments, the unit dosage form comprises an amount of an angiotensin (1-7) peptide suitable for the administration of about 0.5 mg/kg, about 0.6 mg/kg, about 0.7 mg/kg, about 0.8 mg/kg, about 0.9 mg/kg, about 1.0 mg/kg, about 1.1 mg/kg, about 1.2 mg/kg, about 1.3 mg/kg, about 1.4 mg/kg, or about 1.5 mg/kg of the angiotensin (1-7) peptide.

In some embodiments, the angiotensin (1-7) peptide is a peptide of SEQ ID NO:1.

In some embodiments, the angiotensin (1-7) peptide is a functional equivalent of SEQ ID NO:1.

In another aspect, the invention provides a kit comprising any pharmaceutical composition described herein (e.g., any unit dosage form as described herein).

Other features, objects, and advantages of the present invention are apparent in the detailed description that follows. It should be understood, however, that the detailed description, while indicating embodiments of the present invention, is given by way of illustration only, not limitation. Various changes and modifications within the scope of the invention will become apparent to those skilled in the art from the detailed description.

DETAILED DESCRIPTION

The present invention provides, among other things, new methods based on the use of angiotensin (1-7) peptides, analogs or derivatives thereof for treating cardiac disease or disorder in (e.g., non-ambulatory subjects having muscular dystrophy, for example Duchenne muscular dystrophy (DMD) or Becker muscular dystrophy. In some embodiments, treatment methods described herein comprise daily subcutaneous administration of an angiontensin (1-7) peptide (e.g., a compound of SEQ ID NO:1) or a functional equivalent thereof to a subject.

The patent and scientific literature referred to herein establishes knowledge that is available to those of skill in the art. The issued U.S. patents, allowed applications, published U.S. and foreign applications, and references that are cited herein are hereby incorporated by reference to the same extent as if each was specifically and individually indicated to be incorporated by reference.

As used herein, the recitation of a numerical range for a variable is intended to convey that the invention can be practiced with the variable equal to any of the values within that range. Thus, for a variable which is inherently discrete, the variable can be equal to any integer value within the numerical range, including the end-points of the range. Similarly, for a variable which is inherently continuous, the variable can be equal to any real value within the numerical range, including the end-points of the range. As an example, and without limitation, a variable which is described as having values between 0 and 2 can take the values 0, 1 or 2 if the variable is inherently discrete, and can take the values 0.0, 0.1, 0.01, 0.001, or any other real values $\geq 0$ and $\leq 2$ if the variable is inherently continuous.

In order for the present invention to be more readily understood, certain terms are first defined below. Additional definitions for the following terms and other terms are set forth throughout the specification.

As used in this application, the terms "about" and "approximately" are used as equivalents. Any numerals used in this application with or without about/approximately are meant to cover any normal fluctuations appreciated by one of ordinary skill in the relevant art.

Approximately or about: As used herein, the term "approximately" or "about," as applied to one or more values of interest, refers to a value that is similar to a stated reference value. In some embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Biologically active: As used herein, the phrase "biologically active" refers to a characteristic of any agent that has activity in a biological system, and particularly in an organism. For instance, an agent that, when administered to an organism, has a biological effect on that organism, is considered to be biologically active. In particular embodiments, where a peptide is biologically active, a portion of that peptide that shares at least one biological activity of the peptide is typically referred to as a "biologically active" portion. In some embodiments, a peptide has no intrinsic biological activity but that inhibits the effects of one or more naturally-occurring angiotensin compounds is considered to be biologically active.

Carrier or diluent: As used herein, the terms "carrier" and "diluent" refers to a pharmaceutically acceptable (e.g., safe and non-toxic for administration to a human) carrier or diluting substance useful for the preparation of a pharmaceutical formulation. Exemplary diluents include sterile water, bacteriostatic water for injection (BWFI), a pH buffered solution (e.g. phosphate-buffered saline), sterile saline solution, Ringer's solution or dextrose solution.

Dosage form: As used herein, the terms "dosage form" and "unit dosage form" refer to a physically discrete unit of a therapeutic agent for the patient to be treated. Each unit contains a predetermined quantity of active material calculated to produce the desired therapeutic effect. It will be understood, however, that the total dosage of the composition will be decided by the attending physician within the scope of sound medical judgment.

Dosing regimen: A "dosing regimen" (or "therapeutic regimen"), as that term is used herein, is a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which are separated from one another by a time period of the same length; in some embodiments, a dosing regimen comprises a plurality of doses and at least two different time periods separating individual doses. In some embodiments, the therapeutic agent is administered continuously over a predetermined period. In some embodiments, the therapeutic agent is administered once a day (QD) or twice a day (BID).

Functional equivalent or derivative: As used herein, the term "functional equivalent" or "functional derivative" denotes a molecule that retains a biological activity (either function or structural) that is substantially similar to that of the original sequence. A functional derivative or equivalent may be a natural derivative or is prepared synthetically. Exemplary functional derivatives include amino acid sequences having substitutions, deletions, or additions of one or more amino acids, provided that the biological activity of the protein is conserved. The substituting amino acid desirably has chemico-physical properties which are similar to that of the substituted amino acid. Desirable similar chemico-physical properties include, similarities in charge, bulkiness, hydrophobicity, hydrophilicity, and the like.

Improve, increase, or reduce: As used herein, the terms "improve," "increase" or "reduce," or grammatical equivalents, indicate values that are relative to a baseline measurement, such as a measurement in the same individual prior to initiation of the treatment described herein, or a measurement in a control individual (or multiple control individuals) in the absence of the treatment described herein. A "control individual" is an individual afflicted with the same form of disease as the individual being treated, who is about the same age as the individual being treated (to ensure that the stages of the disease in the treated individual and the control individual(s) are comparable).

In vitro: As used herein, the term "in vitro" refers to events that occur in an artificial environment, e.g., in a test tube or reaction vessel, in cell culture, etc., rather than within a multi-cellular organism.

In vivo: As used herein, the term "in vivo" refers to events that occur within a multi-cellular organism, such as a human and a non-human animal. In the context of cell-based systems, the term may be used to refer to events that occur within a living cell (as opposed to, for example, in vitro systems).

Isolated: As used herein, the term "isolated" refers to a substance and/or entity that has been (1) separated from at least some of the components with which it was associated when initially produced (whether in nature and/or in an experimental setting), and/or (2) produced, prepared, and/or manufactured by the hand of man. Isolated substances and/or entities may be separated from at least about 10%, about 20%, about 30%, about 40%, about 50%, about 60%, about 70%, about 80%, about 90%, about 95%, about 98%, about 99%, substantially 100%, or 100% of the other components with which they were initially associated. In some embodiments, isolated agents are more than about 80%, about 85%, about 90%, about 91%, about 92%, about 93%, about 94%, about 95%, about 96%, about 97%, about 98%, about 99%, substantially 100%, or 100% pure. As used herein, a substance is "pure" if it is substantially free of other components. As used herein, the term "isolated cell" refers to a cell not contained in a multi-cellular organism.

Muscular Dystrophy: As used herein, the term "muscular dystrophy" or "MD", refers to a group of diseases that weaken the musculoskeletal system. In some embodiments, a muscular dystrophy is an MD-like condition. In some embodiments, such diseases include progressive wasting of skeletal muscle. In some embodiments, cardiac and smooth muscle are affected.

Prevent: As used herein, the term "prevent" or "prevention", when used in connection with the occurrence of a disease, disorder, and/or condition, refers to reducing the risk of developing the disease, disorder and/or condition. See the definition of "risk."

Polypeptide: The term "polypeptide" as used herein refers a sequential chain of amino acids linked together via peptide bonds. The term is used to refer to an amino acid chain of any length, but one of ordinary skill in the art will understand that the term is not limited to lengthy chains and can refer to a minimal chain comprising two amino acids linked together via a peptide bond. As is known to those skilled in the art, polypeptides may be processed and/or modified.

Protein: The term "protein" as used herein refers to one or more polypeptides that function as a discrete unit. If a single polypeptide is the discrete functioning unit and does not require permanent or temporary physical association with other polypeptides in order to form the discrete functioning unit, the terms "polypeptide" and "protein" may be used interchangeably. If the discrete functional unit is comprised of more than one polypeptide that physically associate with one another, the term "protein" refers to the multiple polypeptides that are physically coupled and function together as the discrete unit.

Risk: As will be understood from context, a "risk" of a disease, disorder, and/or condition comprises a likelihood that a particular individual will develop a disease, disorder, and/or condition (e.g., a muscular dystrophy). In some embodiments, risk is expressed as a percentage. In some embodiments, risk is from 0, 1, 2, 3, 4, 5, 6, 7, 8, 9, 10, 20, 30, 40, 50, 60, 70, 80, 90 up to 100%. In some embodiments risk is expressed as a risk relative to a risk associated with a reference sample or group of reference samples. In some embodiments, a reference sample or group of reference samples have a known risk of a disease, disorder, condition and/or event (e.g., a muscular dystrophy). In some embodiments a reference sample or group of reference samples are from individuals comparable to a particular individual. In some embodiments, relative risk is 0, 1, 2, 3, 4, 5, 6, 7, 8, 9, 10, or more.

Stability: As used herein, the term "stable" refers to the ability of the therapeutic agent to maintain its therapeutic efficacy (e.g., all or the majority of its intended biological activity and/or physiochemical integrity) over extended periods of time. The stability of a therapeutic agent, and the capability of the pharmaceutical composition to maintain stability of such therapeutic agent, may be assessed over extended periods of time (e.g., for at least 1, 3, 6, 12, 18, 24, 30, 36 months or more). In some embodiments, pharmaceutical compositions described herein have been formulated such that they are capable of stabilizing, or alternatively slowing or preventing the degradation, of one or more therapeutic agents formulated therewith. In the context of a formulation a stable formulation is one in which the therapeutic agent therein essentially retains its physical and/or chemical integrity and biological activity upon storage and during processes (such as freeze/thaw, mechanical mixing and lyophilization).

Patient: As used herein, the term "patient" refers to a human presenting to a medical provider for diagnosis or treatment of a disease. The term "subject" is used herein interchangeably with "individual" or "patient." A patient can be afflicted with or is susceptible to a disease or disorder but may or may not display symptoms of the disease or disorder. A patient can be non-ambulatory or ambulatory.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Suffering from: An individual who is "suffering from" a disease, disorder, and/or condition has been diagnosed with or displays one or more symptoms of the disease, disorder, and/or condition.

Susceptible to: An individual who is "susceptible to" a disease, disorder, and/or condition has not been diagnosed with the disease, disorder, and/or condition. In some embodiments, an individual who is susceptible to a disease, disorder, and/or condition may not exhibit symptoms of the disease, disorder, and/or condition. In some embodiments, an individual who is susceptible to a disease, disorder, condition, or event (for example, Muscular Dystrophy) may be characterized by one or more of the following: (1) a genetic mutation associated with development of the disease, disorder, and/or condition; (2) a genetic polymorphism associated with development of the disease, disorder, and/or condition; (3) increased and/or decreased expression and/or activity of a protein associated with the disease, disorder, and/or condition; (4) habits and/or lifestyles associated with development of the disease, disorder, condition, and/or event (5) having undergone, planning to undergo, or requiring a transplant. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

Therapeutically effective amount: As used herein, the term "therapeutically effective amount" of a therapeutic agent means an amount that is sufficient, when administered to a subject suffering from or susceptible to a disease, disorder, and/or condition, to treat, diagnose, prevent, and/or delay the onset of the symptom(s) of the disease, disorder, and/or condition. It will be appreciated by those of ordinary skill in the art that a therapeutically effective amount is typically administered via a dosing regimen comprising at least one unit dose.

Treating: As used herein, the term "treat," "treatment," or "treating" refers to any method used to partially or completely alleviate, ameliorate, relieve, inhibit, prevent, delay onset of, reduce severity of and/or reduce incidence of one or more symptoms or features of a particular disease, disorder, and/or condition. Treatment may be administered to a subject who does not exhibit signs of a disease and/or exhibits only early signs of the disease for the purpose of decreasing the risk of developing pathology associated with the disease.

Exemplary aspects of the invention are described in detail in the following sections. The use of sections is not meant to limit the invention. Each section can apply to any aspect of the invention. In this application, the use of "or" means "and/or" unless stated otherwise.

Muscular Dystrophy

The muscular dystrophies (MD) are a group of more than 30 genetic diseases characterized by progressive weakness and degeneration of the skeletal muscles that control movement. Some forms of MD are seen in infancy or childhood, while others may not appear until middle age or later. The disorders differ in terms of the distribution and extent of muscle weakness (some forms of MD also affect cardiac muscle), age of onset, rate of progression, and pattern of inheritance.

Duchenne Muscular Dystrophy (DMD)

Duchenne muscular dystrophy (DMD) is a recessive X-linked form of muscular dystrophy which results in muscle degeneration and eventual death. DMD is characterized by weakness in the proximal muscles, abnormal gait, hypertrophy in the gastrocnemius (calf) muscles, and elevated creatine kinase. Many DMD patients are diagnosed around the age of 5, when symptoms/signs typically become more obvious. Affected individuals typically stop walking around age 10-13 and die in or before their mid to late 20's due to cardiorespiratory dysfunction.

DMD is caused by a mutation in the dystrophin gene, located on the human X chromosome, which codes for the protein dystrophin, an important structural component within muscle tissue that provides structural stability to the dystroglycan complex (DGC) of the cell membrane. Dystrophin links the internal cytoplasmic actin filament network and extracellular matrix, providing physical strength to muscle fibers. Accordingly, alteration or absence of dystrophin results in abnormal sarcolemnal membrane tearing and necrosis of muscle fibers. While both sexes can carry the mutation, females rarely exhibit severe signs of the disease.

A main symptom of DMD is muscle weakness associated with muscle wasting with the voluntary muscles being affected first typically, especially affecting the muscles of the hips, pelvic area, thighs, shoulders, and calf muscles. Muscle weakness also occurs in the arms, neck, and other areas. Calves are often enlarged. Signs and symptoms usually appear before age 6 and may appear as early as infancy.

Other physical symptoms include, but are not limited to, delayed ability to walk independently, progressive difficulty in walking, stepping, or running, and eventual loss of ability to walk (usually by the age of 12), frequent falls, fatigue; difficulty with motor skills (running, hopping, jumping), increased lumbar lordosis, leading to shortening of the hip-flexor muscles, contractures of Achilles tendon and hamstrings impairing functionality because the muscle fibers shorten and fibrosis occurs in connective tissue, muscle fiber deformities, pseudohypertrophy (enlarging) of tongue and calf muscles caused by replacement of muscle tissue by fat and connective tissue, higher risk of neurobehavioral disorders (e.g., ADHD), learning disorders (dyslexia), and non-progressive weaknesses in specific cognitive skills (in particular short-term verbal memory), skeletal deformities (including scoliosis in some cases).

Progression of DMD (e.g., in subjects who are non-ambulatory) can also manifest in medical conditions such as respiratory, orthopedic, or cardiac diseases or disorders. Accordingly, new, effective methods for the treatment of these medical conditions (e.g., to improve or maintain cardiac function) are needed.

Becker Muscular Dystrophy (BMD)

Becker muscular dystrophy (BMD) is an X-linked recessive inherited disorder characterized by slowly progressive muscle weakness of the legs and pelvis. It is caused by mutations in the dystrophin gene, which encodes the protein dystrophin. Becker muscular dystrophy is related to Duchenne muscular dystrophy in that both result from a mutation in the dystrophin gene. Complications associated with BMD include cardiac arrhythmias, mental impairment, pulmonary failure and pneumonia.

The BMD disorder is inherited with an X-linked recessive inheritance pattern. The gene is located on the X chromosome. Since women have two X chromosomes, if one X chromosome has the non-working gene, the second X chromosome will have a working copy of the gene to compensate. Because of this ability to compensate, women rarely develop BMD symptoms. All dystrophinopathies are inherited in an X-linked recessive manner. The risk to the siblings of an affected individual depends upon the carrier status of the mother. Carrier females have a 50% chance of passing the mutation in each pregnancy. Sons who inherit the mutation will be affected; daughters who inherit the mutation will be carriers. Men who have Becker muscular dystrophy can have children, and all their daughters are carriers, but none of the sons will inherit their father's mutation.

BMD occurs in approximately 1.5 to 6 in 100,000 male births, making it much less common than Duchenne muscular dystrophy. Symptoms usually appear in men at about ages 8-25, but may sometimes begin later. Sons of a man with Becker muscular dystrophy do not develop the disorder, but daughters will be carriers (and some carriers can experience some symptoms of muscular dystrophy), the daughters' sons may develop the disorder.

BMD symptoms include, but are not limited to, muscle weakness, severe upper extremity muscle weakness, slowly progressive difficulty walking, toe-walking, skeletal deformities, difficulty breathing, chest and back (scoliosis), pseudohypertrophy of calf muscles, muscle cramps, elevated creatine kinase levels in blood and heart muscle problems.

Cardiac Diseases and Disorders

Cardiac muscle is different than skeletal muscle. It is therefore not possible to predict the effect of a drug on cardiac muscle from its effect on skeletal muscle.

The present methods and pharmaceutical compositions can be used for the treatment of cardiac diseases or disorders in a patient in need thereof (e.g., a non-ambulatory subject having muscular dystrophy). More than one cardiac disease or disorder can be treated by methods and compositions described herein. In some embodiments, the patient being treated has or has been diagnosed with Duchenne muscular dystrophy (DMD). In some embodiments, the patient being treated has or has been diagnosed with Becker muscular dystrophy.

Exemplary cardiac diseases and disorders include cardiomyopathy, cardiac arrhythmia, heart failure, left ventricular dysfunction (LVD), myocardial fibrosis (MF), or a conduction disorder.

A subject (e.g., a non-ambulatory subject with DMD) having a cardiac disease or disorder may be asymptomatic or symptomatic. Exemplary symptoms include palpitations, dizziness, edema (e.g., peripheral edema), ascites, or pleural effusion, or any combination thereof.

In some embodiments, a cardiac disease or disorder is cardiomyopathy. In some embodiments, cardiomyopathy is dilated cardiomyopathy (DCM) such as ischemic, valvular, genetic, pediatric, or acquired DCM. In some embodiments, cardiomyopathy is left ventricular non-compaction cardiomyopathy (LVNC).

In some embodiments, a cardiac disease or disorder is cardiac arrhythmia. In some embodiments, a cardiac arrhythmia is a ventricular arrhythmia. In some embodiments, a cardiac arrhythmia is an atrial arrhythmia. In some embodiments, a cardiac arrhythmia is sinus tachycardia (e.g., persistent or labile sinus tachycardia), ventricular tachycardia, atrial fibrillation, atrial flutter, atrioventricular block, or sinus sick disease. In some embodiments, there is an abnormality in atrioventricular conduction In some embodiments, a cardiac disease or disorder is myocardial fibrosis (MF).

In some embodiments, a cardiac disease or disorder is heart failure (e.g., chronic heart failure or right-sided heart failure).

In some embodiments, a cardiac disease or disorder is left ventricular dysfunction (LVD). In some embodiments, LVD is low ventricular ejection fraction (e.g., less than or about 55% such as about 35% to about 55%).

Therapeutic effects can be assessed by methods known in the art. For example, cardiac imaging techniques such as cardiac magnetic resonance imaging (CMR) can be used to assess cardiac function. In some embodiments, CMR is used with gadolinium enhancement (e.g., CMR with late gadolinium enhancement). Still other exemplary methods include electrocardiography (ECG) or echocardiography (e.g., Doppler echocardiography), including echocardiography with myocardial strain analysis.

In some embodiments, treatment of a cardiac disease or disorder results in improved cardiac function (e.g., compared to the cardiac function of a subject immediately prior to commencement of treatment).

In some embodiments, treatment of a cardiac disease or disorder results in maintained cardiac function (e.g., compared to the cardiac function of a subject immediately prior to commencement of treatment).

In some embodiments, treatment of a cardiac disease or disorder results in delaying the onset of a cardiac disease or disorder (e.g., compared to the cardiac function of a subject immediately prior to commencement of treatment).

In some embodiments, treatment of a cardiac disease or disorder results in preventing a cardiac disease or disorder (e.g., compared to the cardiac function of a subject immediately prior to commencement of treatment).

In some embodiments, the cardiac disease or disorder is cardiomyopathy.

Cardiomyopathy

Cardiomyopathy is a disease of the heart muscle, which makes it harder for the heart to fill with blood and to pump blood. Cardiomyopathy can lead to heart failure and may require heart transplantation. Cardiomyopathy can also cause abnormal heart rhythms. Genetic testing has increased our understanding of cardiomyopathies and has led to identification of specific genetic mutations that lead to the disease and detect mutation carriers even before the disease begins. Advanced imaging techniques can also identify problems with the heart muscle.

Cardiomyopathies are typically divided into two major groups based on predominant organ involvement (see Maron et al., Circulation 113(14):1807-16 (2006)). Primary cardiomyopathies (genetic, nongenetic, acquired) are those solely or predominantly confined to heart muscle and are relatively few in number. Secondary cardiomyopathies show pathological myocardial involvement as part of a large number and variety of generalized systemic (multiorgan) disorders. The frequency and degree of secondary myocardial involvement vary considerably among these diseases, some of which are exceedingly uncommon and for which the evidence of myocardial pathology may be sparse and reported in only a few patients.

Genetic cardiomyopathies include, but are not limited to, hypertrophic cardiomyopathy (HCM), arrhythmogenic right ventricular cardiomyopathy/dysplasia (ARVC/D), LV noncompaction, conduction system disease, ion channelopathies, Long-QT syndrome, Brugada syndrome, catecholaminergic polymorphic ventricular tachycardia (CPVT), short-QT syndrome (SQTS) and idiopathic ventricular fibrillation.

Hypertrophic Cardiomyopathy (HCM)

Hypertrophic Cardiomyopathy (HCM) is a clinically heterogeneous, but relatively common autosomal dominant genetic heart disease (1:500 of the general population for the disease phenotype recognized by echocardiography) that probably is the most frequently occurring cardiomyopathy.

HCM is typically characterized morphologically and defined by a hypertrophied, nondilated LV in the absence of another systemic or cardiac disease that is capable of producing the magnitude of wall thickening evident (e.g., systemic hypertension, aortic valve stenosis). Clinical diagnosis is customarily made with 2-dimensional echocardiography (or alternatively with cardiac magnetic resonance imaging) by detection of otherwise unexplained LV wall thickening, usually in the presence of a small LV cavity, after suspicion is raised by the clinical profile or as part of family screening.

When LV wall thickness is mild, differential diagnosis with physiological athlete's heart may arise. Furthermore, individuals harboring a genetic defect for HCM do not necessarily express clinical markers of their disease such as LV hypertrophy on echocardiogram, ECG abnormalities, or symptoms at all times during life, and ECG alterations can precede the appearance of hypertrophy. Indeed, virtually any LV wall thickness, even when within normal limits, is consistent with the presence of an HCM-causing mutant gene, and diagnosis can be made by laboratory DNA analysis. Furthermore, recognition of LV hypertrophy may be age related with its initial appearance delayed well into adulthood (adult morphological conversion). Most HCM patients have the propensity to develop dynamic obstruction to LV outflow under resting or physiologically provocable conditions, produced by systolic anterior motion of the mitral valve with ventricular septal contact.

HCM is caused by a variety of mutations encoding contractile proteins of the cardiac sarcomere. Several mutant genes are associated with HCM, most commonly β-myosin heavy chain (the first identified) and myosin-binding protein C. The other genes appear to account for far fewer cases of HCM and include troponin T and I, regulatory and essential myosin light chains, titin, α-tropomyosin, α-actin, α-myosin heavy chain, and muscle LIM protein. This genetic diversity is compounded by considerable intragenic heterogeneity, with >400 individual mutations now identified. These most commonly are missense mutations but include insertions, deletions, and splice (split-site) mutations encoding truncated sarcomeric proteins. The characteristic diversity of the HCM phenotype is attributable to the disease-causing mutations and probably to the influence of modifier genes and environmental factors.

In addition, nonsarcomeric protein mutations in genes involved in cardiac metabolism have been reported to be responsible for primary cardiac glycogen storage diseases in older children and adults with a clinical presentation mimicking (or indistinguishable from) that of sarcomeric HCM. One of these conditions involves the gene encoding the γ-2-regulatory subunit of the AMP-activated protein kinase (PRKAG2), associated with variable degrees of LV hypertrophy and ventricular preexcitation. The other involves the gene encoding lysosome-associated membrane protein 2 (LAMP-2), resulting in Danon-type storage disease. Clinical manifestations are limited largely to the heart, usually with massive degrees of LV hypertrophy and ventricular preexcitation. These disorders are now part of a subgroup of previously described infiltrative forms of LV hypertrophy such as Pompe disease, a glycogen storage disease caused by α-1,4 glycosidase (acid maltase deficiency) in infants, and Fabry's disease, an X-linked recessive disorder of glycosphingolipid metabolism caused by a deficiency of the lysosomal enzyme α-galactosidase A, resulting in intracellular accumulation of glycosphingolipids.

A number of other diseases associated with LV hypertrophy involve prominent thickening of the LV wall, occurring mostly in infants and children ≤4 years of age, which may resemble or mimic typical HCM caused by sarcomere protein mutations. These cardiomyopathies include secondary forms such as Noonan syndrome, an autosomal dominant cardiofacial condition associated with a variety of cardiac defects (most commonly, dysplastic pulmonary valve stenosis and atrial septal defect) resulting from mutations in PTPN11, a gene encoding the nonreceptor protein tyrosine phosphatase SHP-2 genes.

Other diseases in this category include, but are not limited to, mitochondrial myopathies resulting from mutations encoding mitochondrial DNA (including Kearns-Sayre syndrome) or mitochondrial proteins associated with ATP electron transport chain enzyme defects that alter mitochondrial morphology. Also included are metabolic myopathies representing ATP production and utilization defects involving abnormalities of fatty acid oxidation (acyl CoA dehydrogenase deficiencies) and carnitine deficiency, as well as infiltrative myopathies, i.e., glycogen storage diseases (type II; autosomal recessive Pompe disease), Hunter's and Hurler's diseases, and the transient and nonfamilial cardiomyopathy as part of generalized organomegaly, recognized in infants of insulin-dependent diabetic mothers. In older patients, a number of systemic diseases have been associated with hypertrophic forms of cardiomyopathy; these include Friedreich's ataxia, pheochromocytoma, neurofibromatosis, lentiginosis, and tuberous sclerosis.

Arrhythmogenic Right Ventricular Cardiomyopathy/Dysplasia

ARVC/D is form of inheritable heart muscle disease, which involves predominantly the right ventricle with progressive loss of myocytes and fatty or fibrofatty tissue replacement, resulting in regional (segmental) or global abnormalities. Although frequently associated with myocarditis (enterovirus or adenovirus in some cases), ARVC/D is not considered a primary inflammatory cardiomyopathy. In addition, evidence of LV involvement with fibrofatty replacement, chamber enlargement, and myocarditis is reported in up to 75% of patients.

ARVC/D has a broad clinical spectrum, usually presenting clinically with ventricular tachyarrhythmias (e.g., monomorphic ventricular tachycardia). Noninvasive clinical diagnosis may be confounding, without an easily obtained single test or finding that is definitively diagnostic, and generally requires an integrated assessment of electrical, functional, and anatomic abnormalities. Diagnosis often requires a high index of suspicion, frequently triggered by presentation with arrhythmias, syncope, or cardiac arrest, as well as global or segmental chamber dilatation or wall motion abnormalities.

Noninvasive tests used to diagnose ARVC/D, in addition to personal and family history, include 12-lead ECG, echocardiography, right ventricular angiography, cardiac magnetic resonance imaging, and computerized tomography. Endomyocardial biopsy from the right ventricular free wall is a sensitive diagnostic marker when fibrofatty infiltration is associated with surviving strands of myocytes. ECGs most commonly show abnormal repolarization with T-wave inversion in leads V1 through V3 and small-amplitude potentials at the end of the QRS complex (epsilon wave); Brugada syndrome-like right bundle-branch block and right precordial ST-segment elevation accompanied by polymorphic ventricular tachycardia also have been reported in a small subpopulation of ARVC/D patients.

In many cases, ARVC/D shows autosomal dominant inheritance, albeit often with incomplete penetrance. Autosomal dominant ARVC/D has been mapped to 8 chromosomal loci, with mutations identified thus far in 4 genes: the cardiac ryanodine receptor RyR2, which is also responsible for familial catecholaminergic polymorphic ventricular tachycardia (CPVT); desmoplakin; plakophillin-2; and mutations altering regulatory sequences of the transforming growth factor-$\beta$ gene, which has a role in inflammation. Two recessive forms have been described in conjunction with palmoplantar keratoderma and woolly hair (Naxos disease) and with Carvajal syndrome, caused by mutations in junctional plakoglobin and desmoplakin, respectively. Although the function of desmosomal proteins to anchor intermediate filaments to desmosomes implicates ARVC/D as a primary structural abnormality, there is also a link to ion channel dysfunction.

LV Noncompaction

Noncompaction of ventricular myocardium is a congenital cardiomyopathy characterized by a distinctive ("spongy") morphological appearance of the LV myocardium. Noncompaction involves predominantly the distal (apical) portion of the LV chamber with deep intertrabecular recesses (sinusoids) in communication with the ventricular cavity, resulting from an arrest in the normal embryogenesis. LV noncompaction (LVNC) may be an isolated finding or may be associated with other congenital heart anomalies such as complex cyanotic congenital heart disease.

Diagnosis can be made with 2-dimensional echocardiography, cardiac magnetic resonance imaging, or LV angiography. The natural history of LVNC includes LV systolic dysfunction and heart failure (and some cases of heart transplantation), thromboemboli, arrhythmias, sudden death, and diverse forms of remodeling. Both familial and nonfamilial cases have been described. In the isolated form of LVNC, ZASP (Z-line) and mitochondrial mutations and X-linked inheritance resulting from mutations in the G4.5 gene encoding tafazzin (including association with Barth syndrome in neonates) have been reported. Noncompaction associated with congenital heart disease has been shown to result from mutations in the $\alpha$-dystrobrevin gene and transcription factor NKX2.5.

Conduction System Disease

Lenegre disease, also known as progressive cardiac conduction defect, is characterized by primary progressive development of cardiac conduction defects in the His-Purkinje system, leading to widening of the QRS complex, long pauses, and bradycardia that may trigger syncope. Sick sinus syndrome is phenotypically similar to progressive cardiac conduction defect. Familial occurrence of both syndromes has been reported with an autosomal dominant pattern of inheritance. An ion channelopathy, in the form of SCN5A mutations, is thought to contribute to these conduction system defects. Wolff-Parkinson-White syndrome is familial in some cases, but information about the genetic causes is unavailable.

Ion Channelopathies

Some uncommon inherited and congenital arrhythmia disorders are caused by mutations in genes encoding defective ionic channel proteins, governing cell membrane transit of sodium and potassium ions. These ion channel disorders include, but are not limited to, LQTS, short-QT syndrome (SQTS), Brugada syndrome, and CPVT. Nocturnal sudden unexplained death syndrome in young Southeast Asian males and Brugada syndrome are based on similar clinical and genetic profiles. A small proportion (5% to 10%) of sudden infant deaths also may be linked to ion channelopathies, including LQTS, SQTS, and Brugada syndrome. Clinical diagnosis of the ion channelopathies often can be made by identification of the disease phenotype on standard 12-lead ECG.

Long-QT Syndrome (LQTS)

Long-QT Syndrome is characterized by prolongation of ventricular repolarization and QT interval (corrected for heart rate) on the standard 12-lead ECG, a specific form of polymorphic ventricular tachycardia (torsade des pointes), and a risk for syncope and sudden cardiac death. Phenotypic expression (on the ECG) varies considerably, and approximately 25% to 50% of affected family members may show borderline or even normal QT intervals.

Two patterns of inheritance have been described in LQTS: a rare autosomal recessive disease associated with deafness (Jervell and Lange-Nielsen syndrome), which is caused by 2 genes that encode for the slowly activating delayed rectifier potassium channel (KCNQ1 and KCNE1 [minK]), and the much more common autosomal dominant disease unassociated with deafness (Romano-Ward syndrome), which is caused by mutations in 8 different genes. These include KCNQ1 (KvLQT1, LQT1), KCNH2 (HERG, LQT2), SCN5A (Na1.5, LQT3), ANKB (LQT4), KCNE1 (minK, LQT5), KCNE2 (MiRP1, LQT6), KCNJ2 (Kir2.1, LQT7, Andersen's syndrome), and CACNA1C (Ca1.2, LQT8, Timothy syndrome). Of the 8 genes, 6 encode for cardiac potassium channels, 1 for the sodium channel (SCN5A, LQT3), and 1 for the protein ankyrin, which is involved in anchoring ion channels to the cellular membrane (ANKB).

Brugada Syndrome

The Brugada syndrome is associated with sudden cardiac death in young people. The syndrome is identified by a distinctive ECG pattern consisting of right bundle-branch block and coved ST-segment elevation in the anterior precordial leads (V1 through V3). The characteristic ECG pattern is often concealed and may be unmasked with the administration of sodium channel blockers, including ajmaline, flecainide, procainamide, and pilsicainide. Familial autosomal dominant and sporadic forms have been linked to mutations in an α-subunit of the cardiac sodium channel gene SCN5A (the same gene responsible for LQT3) in 20% of patients. Another locus has been reported on the short arm of chromosome 3.

Sudden unexplained nocturnal death syndrome, found predominantly in young Southeast Asian males is a disorder causing sudden death during sleep as a result of ventricular tachycardia/fibrillation. Some cases of sudden unexplained nocturnal death syndrome resulting from SCN5A gene mutations and Brugada syndrome have been shown to be phenotypically, genetically, and functionally the same disorder.

Catecholaminergic Polymorphic Ventricular Tachycardia (CPVT)

CPVT is characterized by syncope, sudden death, polymorphic ventricular tachycardia triggered by vigorous physical exertion or acute emotion (usually in children and adolescents), a normal resting ECG, and the absence of structural cardiac disease. Family history of 1 or multiple sudden cardiac deaths is evident in 30% of cases. The resting ECG is unremarkable, except for sinus bradycardia and prominent U waves in some patients. The most typical arrhythmia of CPVT is bidirectional ventricular tachycardia presenting with an alternating QRS axis. The autosomal dominant form of the disease has been linked to the RyR2 gene encoding for the cardiac ryanodine receptor, a large protein that forms the calcium release channel in the sarcoplasmic reticulum that is essential for regulation of excitation-contraction coupling and intracellular calcium levels. An autosomal recessive form has been linked to CASQ2, a gene that encodes for calsequestrin, a protein that serves as a major calcium-binding protein in the terminal cisternae of the sarcoplasmic reticulum. Calsequestrin is bound to the ryanodine receptor and participates in the control of excitation-contraction coupling.

Short-QT Syndrome (SQTS)

SQTS is characterized by a short QT interval (<330 ms) on an ECG and a high incidence of sudden cardiac death resulting from ventricular tachycardia/fibrillation. Another distinctive ECG feature of SQTS is the appearance of tall peaked T waves similar to those encountered with hyperkalemia. The syndrome has been linked to gain-of-function mutations in KCNH2 (HERG, SQT1), KCNQ1 (KvLQT1, SQT2), and KCNJ2 (Kir2.1, SQT3), causing an increase in the intensity of $I_{Kr}$, $I_{ks}$, and $I_{k1}$, respectively.

Idiopathic Ventricular Fibrillation

A subgroup of patients with sudden death appears in the literature with the designation of idiopathic ventricular fibrillation. However, it is likely that idiopathic ventricular fibrillation is not an independent disease entity but rather a conglomeration of conditions with normal gross and microscopic findings in which arrhythmic risk undoubtedly derives from molecular abnormalities, most likely ion channel mutations.

Angiotensin (1-7) Peptides

The present invention provides, among other things, methods of treating cardiac disease or disorder in (e.g., a non-ambulatory) subject having Duchenne muscular dystrophy (DMD) that include daily subcutaneous administration to a subject an angiotensin (1-7) peptide, including those described herein as well as in U.S. Patent Publication No. 2016/0074464, which is herein incorporated by reference in its entirety.

As used herein, the term "angiotensin (1-7) peptide" refers to both naturally-occurring Angiotensin (1-7) and any functional equivalent, analogue or derivative of naturally-occurring Angiotensin (1-7). As used herein, "peptide" and "polypeptide" are interchangeable terms and refer to two or more amino acids bound together by a peptide bond. As used herein, the terms "peptide" and "polypeptide" include both linear and cyclic peptide. The terms "angiotensin-(1-7)", "Angiotensin-(1-7)", "Ang-(1-7)", and "TXA-127" are used interchangeably.

Naturally-Occurring Angiotensin (1-7)

Naturally-occurring Angiotensin (1-7) (also referred to as Ang-(1-7)) is a seven amino acid peptide shown below:

$$\text{Asp}^1\text{-Arg}^2\text{-Val}^3\text{-Tyr}^4\text{-Ile}^5\text{-His}^6\text{-Pro}^7 \quad \text{(SEQ ID NO: 1)}$$

It is part of the renin-angiotensin system and is converted from a precursor, also known as Angiotensinogen, which is an α-2-globulin that is produced constitutively and released into the circulation mainly by the liver. Angiotensinogen is a member of the serpin family and also known as renin substrate. Human angiotensinogen is 452 amino acids long, but other species have angiotensinogen of varying sizes. Typically, the first 12 amino acids are the most important for angiotensin activity:

$$\text{Asp}^1\text{-Arg}^2\text{-Val}^3\text{-Tyr}^4\text{-Ile}^5\text{-His}^6\text{-Pro}^7\text{-Phe}^8\text{-His}^9\text{-Leu}^{10}\text{-Val}^{11}\text{-Ile}^{12} \quad \text{(SEQ ID NO: 3)}$$

Different types of angiotensin may be formed by the action of various enzymes. For example, Angiotensin (1-7) is generated by action of Angiotensin-converting enzyme 2 (ACE 2).

Ang-(1-7) is an endogenous ligand for Mas receptors. Mas receptors are G-protein coupled receptor containing seven transmembrane spanning regions. As used herein, the term "angiotensin-(1-7) receptor" encompasses the G Protein-Coupled Mas Receptors.

As used herein, the term "naturally-occurring Angiotensin (1-7)" includes any Angiotensin (1-7) peptide purified from natural sources and any recombinantly produced or chemically synthesized peptides that have an amino acid sequence identical to that of the naturally-occurring Angiotensin (1-7).

Functional Equivalents, Analogs or Derivatives of Ang-(1-7)

In some embodiments, an angiotensin (1-7) peptide suitable for the present invention is a functional equivalent of naturally-occurring Ang-(1-7). As used herein, a functional equivalent of naturally-occurring Ang-(1-7) refers to any peptide that shares amino acid sequence identity to the naturally-occurring Ang-(1-7) and retain substantially the same or similar activity as the naturally-occurring Ang-(1-7). For example, in some embodiments, a functional equivalent of naturally-occurring Ang-(1-7) described herein has pro-angiogenic activity as determined using methods described herein or known in the art, or an activity such as nitric oxide release, vasodilation, improved endothelial function, antidiuresis, or one of the other properties discussed herein, that positively impacts angiogenesis. In some embodiments, a functional equivalent of naturally-occurring Ang-(1-7) described herein can bind to or activate an angiotensin-(1-7) receptor (e.g., the G protein-coupled Mas receptor) as determined using various assays described herein or known in the art. In some embodiments, a functional equivalent of Ang-(1-7) is also referred to as an angiotensin (1-7) analogue or derivative, or functional derivative.

Typically, a functional equivalent of angiotensin (1-7) shares amino acid sequence similarity to the naturally-occurring Ang-(1-7). In some embodiments, a functional equivalent of Ang-(1-7) according to the invention contains a sequence that includes at least 3 (e.g., at least 4, at least 5, at least 6, at least 7) amino acids from the seven amino acids that appear in the naturally-occurring Ang-(1-7), wherein the at least 3 (e.g., at least 4, at least 5, at least 6, or at least 7) amino acids maintain their relative positions and/or spacing as they appear in the naturally-occurring Ang-(1-7).

In some embodiments, a functional equivalent of Ang-(1-7) also encompasses any peptide that contains a sequence at least 50% (e.g., at least 60%, 70%, 80%, or 90%) identical to the amino acid sequence of naturally-occurring Ang-(1-7). Percentage of amino acid sequence identity can be determined by alignment of amino acid sequences. Alignment of amino acid sequences can be achieved in various ways that are within the skill in the art, for instance, using publicly available computer software such as BLAST, ALIGN or Megalign (DNASTAR) software. Those skilled in the art can determine appropriate parameters for measuring alignment, including any algorithms needed to achieve maximal alignment over the full length of the sequences being compared. Preferably, the WU-BLAST-2 software is used to determine amino acid sequence identity (Altschul et al., *Methods in Enzymology* 266, 460-480 (1996); http://blast.wustl/edu/blast/README.html). WU-BLAST-2 uses several search parameters, most of which are set to the default values. The adjustable parameters are set with the following values: overlap span=1, overlap fraction=0.125, word threshold (T)=11. HSP score (S) and HSP S2 parameters are dynamic values and are established by the program itself, depending upon the composition of the particular sequence, however, the minimum values may be adjusted and are set as indicated above.

Examples of Ang-(1-7) functional equivalents, analogues and derivatives are described in, e.g., U.S. Patent Application Publication No. 20160074464, which is hereby incorporated by reference. Certain exemplary functional equivalents are described below.

In some embodiments, a functional equivalent, analogue or derivative of Ang-(1-7) is a fragment of the naturally-occurring Ang-(1-7). In some embodiments, a functional equivalent, analogue or derivative of Ang-(1-7) contains amino acid substitutions, deletions and/or insertions in the naturally-occurring Ang-(1-7). Ang-(1-7) functional equivalents, analogues or derivatives can be made by altering the amino acid sequences by substitutions, additions, and/or deletions. For example, one or more amino acid residues within the sequence of the naturally-occurring Ang-(1-7) (SEQ ID NO:1) can be substituted by another amino acid of a similar polarity, which acts as a functional equivalent, resulting in a silent alteration. Substitution for an amino acid within the sequence may be selected from other members of the class to which the amino acid belongs. For example, the positively charged (basic) amino acids include arginine, lysine, and histidine. The nonpolar (hydrophobic) amino acids include leucine, isoleucine, alanine, phenylalanine, valine, proline, tryptophan, and methionine. The uncharged polar amino acids include serine, threonine, cysteine, tyrosine, asparagine, and glutamine. The negatively charged (acid) amino acids include glutamic acid and aspartic acid. The amino acid glycine may be included in either the nonpolar amino acid family or the uncharged (neutral) polar amino acid family. Substitutions made within a family of amino acids are generally understood to be conservative substitutions. For example, the amino acid sequence of a peptide inhibitor can be modified or substituted.

An angiotensin-(1-7) peptide can be of any length. In some embodiments, an angiotensin-(1-7) peptide according to the present invention can contain, for example, from 5-25 amino acid residues, such as 5-20, 5-15 or 5-10 amino acid residues. In some embodiments, an Ang-(1-7) peptide according to the present invention contain 5, 6, 7, 8, 9, 10, 11, 12, 13, 14, 15, 16, 17, 18, 19, 20, 21, 22, 23, 24 or 25 residues.

In some embodiments, an angiotensin-(1-7) peptide contains one or more modifications to increase protease resistance, serum stability and/or bioavailability. In some embodiments, suitable modifications are selected from pegylation, acetylation, glycosylation, biotinylation, substitution with D-amino acid and/or un-natural amino acid, and/or cyclization of the peptide.

As used herein, the term "amino acid," in its broadest sense, refers to any compound and/or substance that can be incorporated into a polypeptide chain. In some embodiments, an amino acid has the general structure $H_2N$—$C(H)(R)$—$COOH$. In some embodiments, an amino acid is a naturally-occurring amino acid. In some embodiments, an amino acid is a synthetic or un-natural amino acid (e.g., α,α-disubstituted amino acids, N-alkyl amino acids); in some embodiments, an amino acid is a D-amino acid; in some embodiments, an amino acid is an L-amino acid. "Standard amino acid" refers to any of the twenty standard amino acids commonly found in naturally occurring peptides including both L- and D-amino acids which are both incorporated in peptides in nature. "Nonstandard" or "unconventional amino acid" refers to any amino acid, other than the standard amino acids, regardless of whether it is prepared synthetically or obtained from a natural source. As used herein, "synthetic or un-natural amino acid" encompasses chemically modified amino acids, including but not limited to salts, amino acid derivatives (such as amides), and/or substitutions. Amino acids, including carboxy- and/or amino-terminal amino acids in peptides, can be modified by methylation, amidation, acetylation, and/or substitution with other chemical groups that can change the peptide's circulating half-life without adversely affecting its activity. Examples of unconventional or un-natural amino acids include, but are not limited to, citrulline, ornithine, norleucine, norvaline, 4-(E)-butenyl-4(R)-methyl-N-methylthreonine (MeBmt), N-methyl-leucine (MeLeu), aminoisobutyric acid, statine, and N-methyl-alanine (MeAla). Amino acids may participate in a disulfide bond. The term "amino acid" is used interchangeably with "amino acid residue," and may refer to a free amino acid and/or to an amino acid residue of a peptide. It will be apparent from the context in which the term is used whether it refers to a free amino acid or a residue of a peptide.

In some embodiments, angiotensin-(1-7) peptides contain one or more L-amino acids, D-amino acids, and/or un-natural amino acids.

In addition to peptides containing only naturally occurring amino acids, peptidomimetics or peptide analogs are also encompassed by the present invention. Peptide analogs are commonly used in the pharmaceutical industry as non-peptide drugs with properties analogous to those of the template peptide. The non-peptide compounds are termed "peptide mimetics" or peptidomimetics (Fauchere et al., *Infect. Immun.* 54:283-287 (1986); Evans et al., *J. Med. Chem.* 30:1229-1239 (1987)). Peptide mimetics that are structurally related to therapeutically useful peptides and may be used to produce an equivalent or enhanced therapeutic or prophylactic effect. Generally, peptidomimetics are structurally similar to the paradigm polypeptide (i.e., a polypeptide that has a biological or pharmacological activity) such as naturally-occurring receptor-binding polypeptides, but have one or more peptide linkages optionally replaced by linkages such as —CH$_2$NH—, —CH$_2$S—, —CH$_2$—CH$_2$—, —CH═CH— (cis and trans), —CH$_2$SO—, —CH(OH)CH$_2$—, —COCH$_2$— etc., by methods well known in the art (Spatola, Peptide Backbone Modifications, Vega Data, 1(3):267 (1983); Spatola et al. *Life Sci.* 38:1243-1249 (1986); Hudson et al. *Int. J. Pept. Res.* 14:177-185 (1979); and Weinstein. B., 1983, Chemistry and Biochemistry, of Amino Acids, Peptides and Proteins, Weinstein eds, Marcel Dekker, New-York,). Such peptide mimetics may have significant advantages over naturally-occurring polypeptides including more economical production, greater chemical stability, enhanced pharmacological properties (e.g., half-life, absorption, potency, efficiency, etc.), reduced antigenicity and others.

Ang-(1-7) peptides also include other types of peptide derivatives containing additional chemical moieties not normally part of the peptide, provided that the derivative retains the desired functional activity of the peptide. Examples of such derivatives include (1) N-acyl derivatives of the amino terminal or of another free amino group, wherein the acyl group may be an alkanoyl group (e.g., acetyl, hexanoyl, octanoyl) an aroyl group (e.g., benzoyl) or a blocking group such as F-moc (fluorenylmethyl-O—CO—); (2) esters of the carboxy terminal or of another free carboxy or hydroxyl group; (3) amide of the carboxy-terminal or of another free carboxyl group produced by reaction with ammonia or with a suitable amine; (4) phosphorylated derivatives; (5) derivatives conjugated to an antibody or other biological ligand and other types of derivatives; and (6) derivatives conjugated to a polyethylene glycol (PEG) chain.

Ang-(1-7) peptides may be obtained by any method of peptide synthesis known to those skilled in the art, including synthetic (e.g., exclusive solid phase synthesis, partial solid phase synthesis, fragment condensation, classical solution synthesis, native-chemical ligation) and recombinant techniques. For example, the peptides or peptides derivatives can be obtained by solid phase peptide synthesis, which in brief, consist of coupling the carboxyl group of the C-terminal amino acid to a resin (e.g., benzhydrylamine resin, chloromethylated resin, hydroxymethyl resin) and successively adding N-alpha protected amino acids. The protecting groups may be any such groups known in the art. Before each new amino acid is added to the growing chain, the protecting group of the previous amino acid added to the chain is removed. Such solid phase synthesis has been disclosed, for example, by Merrifield, *J. Am. Chem. Soc.* 85: 2149 (1964); Vale et al., *Science* 213:1394-1397 (1981), in U.S. Pat. Nos. 4,305,872 and 4,316,891, Bodonsky et al. *Chem. Ind.* (London), 38:1597 (1966); and Pietta and Marshall, *Chem. Comm.* 650 (1970) by techniques reviewed in Lubell et al. "Peptides" Science of Synthesis 21.11, *Chemistry of Amides*. Thieme, Stuttgart, 713-809 (2005). The coupling of amino acids to appropriate resins is also well known in the art and has been disclosed in U.S. Pat. No. 4,244,946. (Reviewed in Houver-Weyl, *Methods of Organic Chemistry*. Vol E22a. Synthesis of Peptides and Peptidomimetics, Murray Goodman, Editor-in-Chief, Thieme. Stuttgart. New York 2002).

Unless defined otherwise, the scientific and technological terms and nomenclature used herein have the same meaning as commonly understood by a person of ordinary skill to which this invention pertains. Generally, the procedures of cell cultures, infection, molecular biology methods and the like are common methods used in the art. Such standard techniques can be found in reference manuals such as, for example, Ausubel et al., *Current Protocols in Molecular Biology*, Wiley Interscience, New York, 2001; and Sambrook et al., *Molecular Cloning: A Laboratory Manual*, 3$^{rd}$ edition, Cold Spring Harbor Laboratory Press, N.Y., 2001.

During any process of the preparation of an Ang-(1-7) peptide, it may be desirable to protect sensitive reactive groups on any of the molecule concerned. This may be achieved by means of conventional protecting groups such as those described in Protective Groups In Organic Synthesis by T. W. Greene & P. G. M. Wuts, 1991, John Wiley and Sons, New-York; and Peptides: chemistry and Biology by Sewald and Jakubke, 2002, Wiley-VCH, Wheinheim p. 142. For example, alpha amino protecting groups include acyl type protecting groups (e.g., trifluoroacetyl, formyl, acetyl), aliphatic urethane protecting groups (e.g., t-butyloxycarbonyl (BOC), cyclohexyloxycarbonyl), aromatic urethane type protecting groups (e.g., fluorenyl-9-methoxy-carbonyl (Fmoc), benzyloxycarbonyl (Cbz), Cbz derivatives) and alkyl type protecting groups (e.g., triphenyl methyl, benzyl). The amino acids side chain protecting groups include benzyl (for Thr and Ser), Cbz (Tyr, Thr, Ser, Arg, Lys), methyl ethyl, cyclohexyl (Asp, His), Boc (Arg, His, Cys) etc. The protecting groups may be removed at a convenient subsequent stage using methods known in the art.

Further, Ang-(1-7) peptides may be synthesized according to the FMOC protocol in an organic phase with protective groups. Desirably, the peptides are purified with a yield of 70% with high-pressure liquid chromatography (HPLC) on a C18 chromatography column and eluted with an acetonitrile gradient of 10-60%. The molecular weight of a peptide can be verified by mass spectrometry (reviewed in Fields, G. B. "Solid-Phase Peptide Synthesis" *Methods in Enzymology*. Vol. 289, Academic Press, 1997).

Alternatively, Ang-(1-7) peptides may be prepared in recombinant systems using, for example, polynucleotide sequences encoding the polypeptides. It is understood that a polypeptide may contain more than one of the above-described modifications within the same polypeptide.

While peptides may be effective in eliciting a biological activity in vitro, their effectiveness in vivo might be reduced by the presence of proteases. Serum proteases have specific substrate requirements. The substrate must have both L-amino acids and peptide bonds for cleavage. Furthermore, exopeptidases, which represent the most prominent component of the protease activity in serum, usually act on the first peptide bond of the peptide and require a free N-terminus (Powell et al., *Pharm. Res.* 10:1268-1273 (1993)). In light of this, it is often advantageous to use modified versions of peptides. The modified peptides retain the structural characteristics of the original L-amino acid peptides that confer the desired biological activity of Ang-(1-7) but are advantageously not readily susceptible to cleavage by protease and/or exopeptidases.

Systematic substitution of one or more amino acids of a consensus sequence with D-amino acid of the same type (e.g., D-lysine in place of L-lysine) may be used to generate more stable peptides. Thus, a peptide derivative or peptidomimetic of the present invention may be all L, all D or mixed D, L peptide, in either forward or reverse order. The presence of an N-terminal or C-terminal D-amino acid increases the in vivo stability of a peptide since peptidases cannot utilize a D-amino acid as a substrate (Powell et al., *Pharm. Res.* 10:1268-1273 (1993)). Reverse-D peptides are peptides containing D-amino acids, arranged in a reverse sequence relative to a peptide containing L-amino acids. Thus, the C-terminal residue of an L-amino acid peptide becomes N-terminal for the D-amino acid peptide, and so forth. Reverse D-peptides retain the same secondary conformation and therefore similar activity, as the L-amino acid peptides, but are more resistant to enzymatic degradation in vitro and in vivo, and thus can have greater therapeutic efficacy than the original peptide (Brady and Dodson, *Nature* 368:692-693 (1994); Jameson et al., *Nature* 368:744-746 (1994)). Similarly, a reverse-L peptide may be generated using standard methods where the C-terminus of the parent peptide becomes takes the place of the N-terminus of the reverse-L peptide. It is contemplated that reverse L-peptides of L-amino acid peptides that do not have significant secondary structure (e.g., short peptides) retain the same spacing and conformation of the side chains of the L-amino acid peptide and therefore often have the similar activity as the original L-amino acid peptide. Moreover, a reverse peptide may contain a combination of L- and D-amino acids. The spacing between amino acids and the conformation of the side chains may be retained resulting in similar activity as the original L-amino acid peptide.

Another effective approach to confer resistance to peptidases acting on the N-terminal or C-terminal residues of a peptide is to add chemical groups at the peptide termini, such that the modified peptide is no longer a substrate for the peptidase. One such chemical modification is glycosylation of the peptides at either or both termini. Certain chemical modifications, in particular N-terminal glycosylation, have been shown to increase the stability of peptides in human serum (Powell et al., *Pharm. Res.* 10:1268-1273 (1993)). Other chemical modifications which enhance serum stability include, but are not limited to, the addition of an N-terminal alkyl group, consisting of a lower alkyl of from one to twenty carbons, such as an acetyl group, and/or the addition of a C-terminal amide or substituted amide group. In particular, the present invention includes modified peptides consisting of peptides bearing an N-terminal acetyl group and/or a C-terminal amide group.

Substitution of non-naturally-occurring amino acids for natural amino acids in a subsequence of the peptides can also confer resistance to proteolysis. Such a substitution can, for instance, confer resistance to proteolysis by exopeptidases acting on the N-terminus without affecting biological activity. Examples of non-naturally-occurring amino acids include α,α-disubstituted amino acids, N-alkyl amino acids, C-α-methyl amino acids, β-amino acids, and β-methyl amino acids. Amino acids analogs useful in the present invention may include, but are not limited to, β-alanine, norvaline, norleucine, 4-aminobutyric acid, orithine, hydroxyproline, sarcosine, citrulline, cysteic acid, cyclohexylalanine, 2-aminoisobutyric acid, 6-aminohexanoic acid, t-butylglycine, phenylglycine, o-phosphoserine, N-acetyl serine, N-formylmethionine, 3-methylhistidine and other unconventional amino acids. Furthermore, the synthesis of peptides with non-naturally-occurring amino acids is routine in the art.

In addition, constrained peptides comprising a consensus sequence or a substantially identical consensus sequence variation may be generated by methods well known in the art (Rizo and Gierasch, *Ann. Rev. Biochem.* 61:387-418 (1992)). For example, constrained peptides may be generated by adding cysteine residues capable of forming disulfide bridges and, thereby, resulting in a cyclic peptide. Cyclic peptides can be constructed to have no free N- or C-termini. Accordingly, they are not susceptible to proteolysis by exopeptidases, although they may be susceptible to endopeptidases, which do not cleave at peptide termini. The amino acid sequences of the peptides with N-terminal or C-terminal D-amino acids and of the cyclic peptides are usually identical to the sequences of the peptides to which they correspond, except for the presence of N-terminal or C-terminal D-amino acid residue, or their circular structure, respectively.

Cyclic Peptides

In some embodiments, a functional equivalent, analogue or derivative of naturally-occurring Ang-(1-7) is a cyclic peptide. As used herein, a cyclic peptide has an intramolecular covalent bond between two non-adjacent residues. The intramolecular bond may be a backbone to backbone, side-chain to backbone or side-chain to side-chain bond (i.e., terminal functional groups of a linear peptide and/or side-chain functional groups of a terminal or interior residue may be linked to achieve cyclization). Typical intramolecular bonds include disulfide, amide and thioether bonds. A variety of means for cyclizing polypeptides are well known in the art, as are many other modifications that can be made to such peptides. For a general discussion, see International Patent Publication Nos. WO 01/53331 and WO 98/02452, the contents of which are incorporated herein by reference. Such cyclic bonds and other modifications can also be applied to the cyclic peptides and derivative compounds of this invention.

Cyclic peptides as described herein may comprise residues of L-amino acids, D-amino acids, or any combination thereof. Amino acids may be from natural or non-natural sources, provided that at least one amino group and at least one carboxyl group are present in the molecule; α- and β-amino acids are generally preferred. Cyclic peptides may also contain one or more rare amino acids (such as 4-hydroxyproline or hydroxylysine), organic acids or amides and/or derivatives of common amino acids, such as amino acids having the C-terminal carboxylate esterified (e.g., benzyl, methyl or ethyl ester) or amidated and/or having modifications of the N-terminal amino group (e.g., acetylation or alkoxycarbonylation), with or without any of a wide variety of side-chain modifications and/or substitutions (e.g., methylation, benzylation, t-butylation, tosylation, alkoxycarbonylation, and the like). Suitable derivatives include amino acids having an N-acetyl group (such that the amino group that represents the N-terminus of the linear peptide prior to cyclization is acetylated) and/or a C-terminal amide group (i.e., the carboxy terminus of the linear peptide prior to cyclization is amidated). Residues other than common amino acids that may be present with a cyclic peptide include, but are not limited to, penicillamine, β,β-tetramethylene cysteine, β,β-pentamethylene cysteine, β-mercaptopropionic acid, β,β-pentamethylene-β-mercaptopropionic acid, 2-mercaptobenzene, 2-mercaptoaniline, 2-mercaptoproline, ornithine, diaminobutyric acid, α-aminoadipic acid, m-aminomethylbenzoic acid and α,β-diaminopropionic acid.

Following synthesis of a linear peptide, with or without N-acetylation and/or C-amidation, cyclization may be achieved by any of a variety of techniques well known in the art. Within one embodiment, a bond may be generated between reactive amino acid side chains. For example, a disulfide bridge may be formed from a linear peptide comprising two thiol-containing residues by oxidizing the peptide using any of a variety of methods. Within one such method, air oxidation of thiols can generate disulfide linkages over a period of several days using either basic or neutral aqueous media. The peptide is used in high dilution to minimize aggregation and intermolecular side reactions. Alternatively, strong oxidizing agents such as $I_2$ and $K_3Fe(CN)_6$ can be used to form disulfide linkages. Those of ordinary skill in the art will recognize that care must be taken not to oxidize the sensitive side chains of Met, Tyr, Trp or His. Within further embodiments, cyclization may be achieved by amide bond formation. For example, a peptide bond may be formed between terminal functional groups (i.e., the amino and carboxy termini of a linear peptide prior to cyclization). Within another such embodiment, the linear peptide comprises a D-amino acid. Alternatively, cyclization may be accomplished by linking one terminus and a residue side chain or using two side chains, with or without an N-terminal acetyl group and/or a C-terminal amide. Residues capable of forming a lactam bond include lysine, ornithine (Orn), α-amino adipic acid, m-aminomethylbenzoic acid, α,β-diaminopropionic acid, glutamate or aspartate. Methods for forming amide bonds are generally well known in the art. Within one such method, carbodiimide-mediated lactam formation can be accomplished by reaction of the carboxylic acid with DCC, DIC, ED AC or DCCI, resulting in the formation of an O-acylurea that can be reacted immediately with the free amino group to complete the cyclization. Alternatively, cyclization can be performed using the azide method, in which a reactive azide intermediate is generated from an alkyl ester via a hydrazide. Alternatively, cyclization can be accomplished using activated esters. The presence of electron withdrawing substituents on the alkoxy carbon of esters increases their susceptibility to aminolysis. The high reactivity of esters of p-nitrophenol, N-hydroxy compounds and polyhalogenated phenols has made these "active esters" useful in the synthesis of amide bonds. Within a further embodiment, a thioether linkage may be formed between the side chain of a thiol-containing residue and an appropriately derivatized α-amino acid. By way of example, a lysine side chain can be coupled to bromoacetic acid through the carbodiimide coupling method (DCC, EDAC) and then reacted with the side chain of any of the thiol containing residues mentioned above to form a thioether linkage. In order to form dithioethers, any two thiol containing side-chains can be reacted with dibromoethane and diisopropylamine in DMF.

Exemplary Angiotensin-(1-7) Peptides

Exemplary angiotensin (1-7) peptides include linear angiotensin-(1-7) peptides. As discussed above, the structure of naturally-occurring Ang-(1-7) is as follows: $Asp^1$-$Arg^2$-$Val^3$-$Tyr^4$-$Ile^5$-$His^6$-$Pro^7$ (SEQ ID NO:1).

The peptides and peptide analogs of the invention can be generally represented by the following sequence:

(SEQ ID NO: 4)
$Xaa^1$-$Xaa^2$-$Xaa^3$-$Xaa^4$-$Xaa^5$-$Xaa^6$-$Xaa^7$, or a pharmaceutically acceptable salt thereof.

$Xaa^1$ is any amino acid or a dicarboxylic acid. In some embodiments, $Xaa^1$ is Asp, Glu, Asn, Acpc (1-aminocyclopentane carboxylic acid), Ala, Me₂Gly (N,N-dimethylglycine), Pro, Bet (betaine, 1-carboxy-N,N,N-trimethylmethanaminium hydroxide), Glu, Gly, Asp, Sar (sarcosine) or Suc (succinic acid). In certain such embodiments, $Xaa^1$ is a negatively-charged amino acid, such as Asp or Glu, typically Asp.

$Xaa^2$ is Arg, Lys, Ala, Cit (citrulline), Orn (ornithine), acetylated Ser, Sar, D-Arg and D-Lys. In some embodiments, $Xaa^2$ is a positively-charged amino acid such as Arg or Lys, typically Arg.

$Xaa^3$ is Val, Ala, Leu, Nle (norleucine), Ile, Gly, Lys, Pro, HydroxyPro (hydroxyproline), Aib (2-aminoisobutyric acid), Acpc or Tyr. In some embodiments, $Xaa^3$ is an aliphatic amino acid such as Val, Leu, Ile or Nle, typically Val or Nle.

$Xaa^4$ is Tyr, Tyr($PO_3$), Thr, Ser, homoSer (homoserine), azaTyr (aza-α¹-homo-L-tyrosine) or Ala. In some embodiments, $Xaa^4$ is a hydroxyl-substituted amino acid such as Tyr, Ser or Thr, typically Tyr.

$Xaa^5$ is Ile, Ala, Leu, norLeu, Val or Gly. In some embodiments, $Xaa^5$ is an aliphatic amino acid such as Val, Leu, Ile or Nle, typically Ile.

$Xaa^6$ is His, Arg or 6-$NH_2$-Phe (6-aminophenylalanine). In some embodiments, $Xaa^6$ is a fully or partially positively-charged amino acid such as Arg or His.

$Xaa^7$ is Cys, Pro or Ala.

In some embodiments, one or more of $Xaa^1$-$Xaa^7$ is identical to the corresponding amino acid in naturally-occurring Ang-(1-7). In certain such embodiments, all but one or two of $Xaa^1$-$Xaa^7$ are identical to the corresponding amino acid in naturally-occurring Ang-(1-7). In other embodiments, all of $Xaa^1$-$Xaa^6$ are identical to the corresponding amino acid in naturally-occurring Ang-(1-7).

In some embodiments, $Xaa^3$ is Nle. When $Xaa^3$ is Nle, one or more of $Xaa^1$-$Xaa^2$ and $Xaa^{4-7}$ are optionally identical to the corresponding amino acid in naturally-occurring Ang-(1-7). In certain such embodiments, all but one or two of $Xaa^1$-$Xaa^2$ and $Xaa^{4-7}$ are identical to the corresponding amino acid in naturally-occurring Ang-(1-7). In other embodiments, all of $Xaa^1$-$Xaa^2$ and $Xaa^{4-7}$ are identical to the corresponding amino acid in naturally-occurring Ang-(1-7), resulting in the amino acid sequence: $Asp^1$-$Arg^2$-$Nle^3$-$Tyr^4$-$Ile^5$-$His^6$-$Pro^7$ (SEQ ID NO: 5).

In some embodiments, the peptide has the amino acid sequence $Asp^1$-$Arg^2$-$Val^3$-$Ser^4$-$Ile^5$-$His^6$-$Cys^7$ (SEQ ID NO: 2) or $Asp^1$-$Arg^2$-$Val^3$-$ser^4$-$Ile^5$-$His^6$-$Cys^7$ (SEQ ID NO: 6).

Pharmaceutical Compositions

In accordance with the methods of the invention, an angiotensin (1-7) peptide or angiotensin (1-7) receptor agonist as described herein can be administered to a subject alone (e.g., as a purified peptide or compound), or as a component of a pharmaceutical composition or medicament (e.g., in the manufacture of a medicament for the treatment of the disease), as described herein.

In some embodiments, a pharmaceutical composition (e.g., a unit dosage form) is formulated for subcutaneous administration.

Methods of formulating compositions are known in the art (see, e.g., Remington's Pharmaceuticals Sciences, 17th Edition, Mack Publishing Co., (Alfonso R. Gennaro, editor) (1989)).

Exemplary formulations for subcutaneous administration include: aqueous solutions, oily solutions, suspensions, simple emulsions, biodegradable in situ implants, biodegradable microspheres, osmotically controlled implants, dendrimers, liposomes, and lipid nanoparticles.

The compositions can be formulated with a physiologically acceptable carrier or excipient to prepare a pharmaceutical composition. The carrier and composition can be sterile.

Suitable pharmaceutically acceptable excipients include but are not limited to water, salt solutions (e.g., NaCl), saline, buffered saline, alcohols, glycerol, ethanol, gum arabic, vegetable oils, benzyl alcohols, polyethylene glycols, gelatin, carbohydrates such as lactose, amylose or starch, sugars such as mannitol, sucrose, or others, dextrose, magnesium stearate, talc, silicic acid, viscous paraffin, perfume oil, fatty acid esters, hydroxymethylcellulose, polyvinyl pyrolidone, etc., as well as combinations thereof.

A pharmaceutical preparation can, if desired, be mixed with auxiliary agents (e.g., lubricants, preservatives, stabilizers, wetting agents, emulsifiers, salts for influencing osmotic pressure, buffers, coloring, flavoring and/or aromatic substances and the like) which do not deleteriously react with the active compounds or interference with their activity. In a preferred embodiment, a water-soluble carrier suitable for intravenous administration is used. A composition or medicament, if desired, can also contain minor amounts of wetting or emulsifying agents, or pH buffering agents, some of which are further discussed below.

A composition or medicament can be formulated in accordance with the routine procedures as a pharmaceutical composition adapted for administration to human beings. For example, in a preferred embodiment, a composition for intravenous administration typically is a solution in sterile isotonic aqueous buffer. Where necessary, the composition may also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where the composition is to be administered by infusion, it can be dispensed with an infusion bottle containing sterile pharmaceutical grade water, saline or dextrose/water. Where the composition is administered by injection, an ampule of sterile water for injection or saline can be provided so that the ingredients may be mixed prior to administration.

In some embodiments, provided compositions, including those provided as pharmaceutical formulations, comprise a liquid carrier such as but not limited to water, saline, phosphate buffered saline, Ringer's solution, dextrose solution, serum-containing solutions, Hank's solution, other aqueous physiologically balanced solutions, oils, esters and glycols.

An angiotensin (1-7) peptide or angiotensin (1-7) receptor agonist as described herein can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

Routes of Administration

An angiotensin (1-7) peptide can be administered subcutaneously. As used herein, the term "subcutaneous tissue", is defined as a layer of loose, irregular connective tissue immediately beneath the skin. For example, the subcutaneous administration may be performed by injecting a composition into areas including, but not limited to, thigh region, abdominal region, gluteal region, or scapular region.

However, more than one route can be used concurrently, if desired. In some embodiments, an angiotensin (1-7) peptide or angiotensin (1-7) receptor agonist as described herein is administered intravenously. In other embodiments, an angiotensin (1-7) peptide or angiotensin (1-7) receptor agonist as described herein is administered by direct administration to a target tissue, such as heart or muscle (e.g., intramuscular), tumor (intratumorally), nervous system (e.g., direct injection into the brain; intraventricularly; intrathecally). Alternatively, an angiotensin (1-7) peptide or angiotensin (1-7) receptor agonist as described herein (or a composition or medicament containing an angiotensin (1-7) peptide or angiotensin (1-7) receptor agonist as described herein) can be administered by inhalation, parenterally, intradermally, transdermally, or transmucosally (e.g., orally or nasally). In some embodiments, an angiotensin (1-7) peptide or angiotensin (1-7) receptor agonist as described herein is administered orally. In some embodiments, the present invention provides solid dosage forms of an angiotensin (1-7) peptide or angiotensin (1-7) receptor agonist as described herein for oral administration including (a) an angiotensin (1-7) peptide, (b) at least one pharmaceutically acceptable pH-lowering agent, (c) at least one absorption enhancer effective to promote bioavailability of the angiotensin (1-7) peptide, and (d) a protective vehicle. In some embodiments, the solid dosage form is a capsule or tablet. Various methods and ingredients for making oral formulations are known in the art and it is expected that one of skill would be able to determine which of these methods and ingredients will be compatible with the invention as described in this specification and/or in U.S. Provisional Patent Application Ser. No. 61/701,972, filed on Sep. 17, 2012, the disclosure of which is hereby incorporated in its entirety. Such methods and ingredients are also contemplated as within the scope of the present invention.

Dosing

In some embodiments, a composition is administered in a therapeutically effective amount and/or according to a dosing regimen that is correlated with a particular desired outcome (e.g., treating a cardiac disease or disorder as described herein).

In some embodiments, a formulation comprising an angiotensin (1-7) peptide or angiotensin (1-7) receptor agonist as described herein is administered as a single dose. In some embodiments, a formulation comprising an angiotensin (1-7) peptide (e.g., a compound of SEQ ID NO:1) or a functional derivative thereof as described herein is administered at regular intervals. Administration at an "interval," as used herein, indicates that the therapeutically effective amount is administered periodically (as distinguished from a one-time dose). The interval can be determined by standard clinical techniques. In some embodiments, a formulation comprising an angiotensin (1-7) peptide (e.g., a compound of SEQ ID NO:1) or a functional derivative thereof as described herein is administered once daily. In some embodiments, a formulation comprising an angiotensin (1-7) peptide (e.g., a compound of SEQ ID NO:1) or a functional derivative thereof as described herein is administered bimonthly, monthly, twice monthly, triweekly, biweekly, weekly, twice weekly, thrice weekly, daily, twice daily, or every six hours.

The administration interval for a single individual need not be a fixed interval, but can be varied over time, depending on the needs of the individual.

As used herein, the term "bimonthly" means administration once per two months (i.e., once every two months); the term "monthly" means administration once per month; the term "triweekly" means administration once per three weeks (i.e., once every three weeks); the term "biweekly" means administration once per two weeks (i.e., once every two weeks); the term "weekly" means administration once per week; and the term "daily" means administration once per day unless otherwise indicated.

In some embodiments, repeat doses are given at the same time of day (e.g. 10 am). In some embodiments, repeat doses are given at different times of day.

In some embodiments, a pharmaceutical composition (e.g., a unit dosage form) comprising an angiotensin (1-7) peptide (e.g., a compound of SEQ ID NO:1) or a functional derivative thereof as described herein is administered at regular intervals indefinitely. In some embodiments, a pharmaceutical composition (e.g., a unit dosage form) comprising an angiotensin (1-7) peptide (e.g., a compound of SEQ ID NO:1) or a functional derivative thereof as described herein is administered at regular intervals for a defined period.

In some embodiments, a pharmaceutical composition (e.g., a unit dosage form) comprising an angiotensin (1-7) peptide (e.g., a compound of SEQ ID NO:1) or a functional derivative thereof as described herein is administered at regular intervals (e.g., once daily) for 5 years, 4, years, 3, years, 2, years, 1 year, 11 months, 10 months, 9 months, 8 months, 7 months, 6 months, 5 months, 4 months, 3 months, 2 months, a month, 3 weeks, 2, weeks, a week, 6 days, 5 days, 4 days, 3 days, 2 days or a day.

In some embodiments, a pharmaceutical composition (e.g., a unit dosage form) comprising an angiotensin (1-7) peptide (e.g., a compound of SEQ ID NO:1) or a functional derivative thereof as described herein is administered at regular intervals (e.g., once daily) for at least 5 years, 4, years, 3, years, 2, years, 1 year, 11 months, 10 months, 9 months, 8 months, 7 months, 6 months, 5 months, 4 months, 3 months, 2 months, a month, 3 weeks, 2, weeks, a week, 6 days, 5 days, 4 days, 3 days, 2 days or a day.

In some embodiments, a pharmaceutical composition (e.g., a unit dosage form) comprising an angiotensin (1-7) peptide (e.g., a compound of SEQ ID NO:1) or a functional derivative thereof as described herein is administered at regular intervals (e.g., once daily) for a period that is about one month to about one year or for a period that is at least about one month to at least about one year.

In some embodiments, a pharmaceutical composition (e.g., a unit dosage form) comprising an angiotensin (1-7) peptide (e.g., a compound of SEQ ID NO:1) or a functional derivative thereof as described herein is administered at regular intervals (e.g., once daily) for about one month, about two months, about three months, about four months, about five months, about six months, about seven months, about eight months, about nine months, about ten months, about eleven months, or about twelve months.

In some embodiments, a pharmaceutical composition (e.g., a unit dosage form) comprising an angiotensin (1-7) peptide (e.g., a compound of SEQ ID NO:1) or a functional derivative thereof as described herein is administered at regular intervals (e.g., once daily) for about one year.

In some embodiments, a pharmaceutical composition (e.g., a unit dosage form) comprising an angiotensin (1-7) peptide (e.g., a compound of SEQ ID NO:1) or a functional derivative thereof as described herein is administered at regular intervals (e.g., once daily) for at least about one month, about two months, about three months, about four months, about five months, about six months, about seven months, about eight months, about nine months, about ten months, about eleven months, or about twelve months.

In some embodiments, a pharmaceutical composition (e.g., a unit dosage form) comprising an angiotensin (1-7) peptide (e.g., a compound of SEQ ID NO:1) or a functional derivative thereof as described herein is administered at regular intervals (e.g., once daily) for at least about one year.

Particular doses or amounts to be administered in accordance with the present invention may vary, for example, depending on the nature and/or extent of the desired outcome, on particulars of route and/or timing of administration, and/or on one or more characteristics (e.g., weight, age, personal history, genetic characteristic, lifestyle parameter, severity of cardiac defect and/or level of risk of cardiac defect, etc., or combinations thereof). Such doses or amounts can be determined by those of ordinary skill.

In various embodiments, an angiotensin (1-7) peptide (e.g., a compound of SEQ ID NO:1) or a functional derivative thereof is administered at a therapeutically effective amount. As used herein, the term "therapeutically effective amount" is largely determined based on the total amount of the therapeutic agent contained in the pharmaceutical compositions (e.g., unit dosage forms) of the present invention. Generally, a therapeutically effective amount is sufficient to achieve a meaningful benefit to the subject (e.g., treating, modulating, curing, preventing and/or ameliorating a disease or condition). In some particular embodiments, appropriate doses or amounts to be administered may be extrapolated from dose-response curves derived from in vitro or animal model test systems.

Therapeutically effective dosage amounts of an angiotensin (1-7) peptide (e.g., a compound of SEQ ID NO:1) or a functional derivative thereof may be present in varying amounts in various embodiments. In some embodiments, a therapeutically effective dosage amount can be, for example, about 0.1 mg/kg to about 10 mg/kg, about 0.1 to about 5.0 mg/kg or about 0.5 to about 2.5 mg/kg. In some embodiments, the therapeutically effective dosage amount can be, for example, about: 0.1 mg/kg, 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1.0 mg/kg, 1.1 mg/kg, 1.2 mg/kg, 1.3 mg/kg, 1.4 mg/kg, 1.5 mg/kg, 1.6 mg/kg, 1.7 mg/kg, 1.8 mg/kg, 1.9 mg/kg, or 2.0 mg/kg.

In some embodiments, a therapeutically effective dosage amounts of an angiotensin (1-7) peptide (e.g., a compound of SEQ ID NO:1) or a functional derivative thereof is 1 mg/kg.

In some embodiments, a therapeutically effective dosage amounts of an angiotensin (1-7) peptide (e.g., a compound of SEQ ID NO:1) or a functional derivative thereof is 1.5 mg/kg. In some embodiments, a therapeutically effective dosage amounts of an angiotensin (1-7) peptide (e.g., a compound of SEQ ID NO:1) or a functional derivative thereof is 2 mg/kg. In some embodiments, a therapeutically effective dosage amounts of an angiotensin (1-7) peptide (e.g., a compound of SEQ ID NO:1) or a functional derivative thereof is 4 mg/kg. In some embodiments, a therapeutically effective dosage amounts of an angiotensin (1-7) peptide (e.g., a compound of SEQ ID NO:1) or a functional derivative thereof is 0.5 mg/kg.

An effective dose for a particular individual can be varied (e.g., increased or decreased) over time, depending on the needs of the individual.

In some embodiments, the patient weighs 20, 25, 30, 35, 40, 45, 50, 55, 60, 65, 70, 75, 80, 85, 90, 95, 100, 105, 110, 115, 120, 125, 130, 135, 140, 145 or 150 kg. An absolute dose of an angiotensin (1-7) peptide (e.g., a compound of SEQ ID NO:1) or a functional derivative thereof for such patient can be calculated based on the patient's weight.

Combination Therapy

In some embodiments, an angiotensin (1-7) peptide (e.g., a compound of SEQ ID NO:1) or a functional derivative thereof is administered in combination with one or more known therapeutic agents (e.g. anti-muscular dystrophy medications or a medication for a cardiac disease or disorder).

In some embodiments, a treatment with one or more known therapeutic agents (e.g. anti-muscular dystrophy medications or a medication for a cardiac disease or disorder) commenced prior to the treatment with an angiotensin (1-7) peptide (e.g., a compound of SEQ ID NO:1) or a functional derivative thereof. In some embodiments, a treatment with one or more known therapeutic agents (e.g. anti-muscular dystrophy medications or a medication for a cardiac disease or disorder) commenced concurrently with the treatment with an angiotensin (1-7) peptide (e.g., a compound of SEQ ID NO:1) or a functional derivative thereof. a treatment with one or more known therapeutic agents (e.g. anti-muscular dystrophy medications or a medication for a cardiac disease or disorder) commenced after the treatment with an angiotensin (1-7) peptide (e.g., a compound of SEQ ID NO:1) or a functional derivative thereof.

In some embodiments, treatment with one or more known therapeutic agents (e.g. anti-muscular dystrophy medications or a medication for a cardiac disease or disorder) occurs throughout a treatment regimen with an angiotensin (1-7) peptide (e.g., a compound of SEQ ID NO:1) or a functional derivative thereof. In some embodiments, treatment with one or more known therapeutic agents (e.g. anti-muscular dystrophy medications or a medication for a cardiac disease or disorder) occurs for part of a treatment regimen with an angiotensin (1-7) peptide (e.g., a compound of SEQ ID NO:1) or a functional derivative thereof.

In some embodiments, the known therapeutic agent(s) is/are administered according to its standard or approved dosing regimen and/or schedule. In some embodiments, the known therapeutic agent(s) is/are administered according to a regimen that is altered as compared with its standard or approved dosing regimen and/or schedule. In some embodiments, such an altered regimen differs from the standard or approved dosing regimen in that one or more unit doses is altered (e.g., reduced or increased) in amount, and/or in that dosing is altered in frequency (e.g., in that one or more intervals between unit doses is expanded, resulting in lower frequency, or is reduced, resulting in higher frequency).

In some embodiments, the angiotensin (1-7) peptide (e.g., a compound of SEQ ID NO:1) or a functional derivative thereof is administered in combination with one or more anti-muscular dystrophy medications. In some embodiments, the one or more anti-muscular dystrophy medications is a glucocorticoids (e.g. prednisone or VBP15), a phosphodiesterase type 5 (pde5) inhibitor, or other therapy such as nitric oxide boosting medications (e.g. HCT 1026 or NCX 320), drisapersen, anti-sense oligonucleotides (e.g. AVI-4658), and others. In some embodiments, the one or more anti-muscular dystrophy medications is selected from the group consisting of Eteplirsen (AVI-4658), HCT 1026, NCX 320 sildenafil, tadalafil, vardenafil, avanafil, iodenafil, mirodenafil, udenafil, zaprinast, a corticosteroid, and combinations thereof. In some embodiments, an angiotensin (1-7) peptide (e.g., a compound of SEQ ID NO:1) or a functional derivative thereof is administered simultaneously with one or more anti-muscular dystrophy medications. In some embodiments, an angiotensin (1-7) peptide (e.g., a compound of SEQ ID NO:1) or a functional derivative thereof and the one or more anti-muscular dystrophy medications are administered sequentially.

In some embodiments, an angiotensin (1-7) peptide (e.g., a compound of SEQ ID NO:1) or a functional derivative thereof is administered in combination with one or more medications for treatment of a cardiac disease or disorder. In some embodiments, the medication treats a different cardiac disease or disorder than the cardiac disease or disorder that is treated by an angiotensin (1-7) peptide (e.g., a compound of SEQ ID NO:1) or a functional derivative thereof. Exemplary medications for treatment of a cardiac disease or disorder that can be administered in combination with an angiotensin (1-7) peptide (e.g., a compound of SEQ ID NO:1) or a functional derivative thereof include: ACE inhibitors (e.g., enalapril, lisinopril, or perindopril), angiotensin-receptor blockers (e.g., losartan), beta blockers (e.g., metoprolol or carvedilol), diuretics (e.g., furosemide or a thiazide), aldosterone receptor antagonists (e.g., spironolactone or eplerenone), vasodilators, or anti-coagulants (e.g., coumadin or aspirin), or any combination thereof.

Kits

The present invention further provides kits or other articles of manufacture which contains an angiotensin (1-7) peptide (e.g., a compound of SEQ ID NO:1) or a functional derivative thereof, or a pharmaceutical composition (e.g., a unit dosage form) comprising the same, and provides instructions for its reconstitution (if lyophilized) and/or use. Kits or other articles of manufacture may include a container, a syringe, vial and any other articles, devices or equipment useful in administration (e.g., subcutaneous, oral, by inhalation). Suitable containers include, for example, bottles, vials, syringes (e.g., pre-filled syringes), ampules, cartridges, reservoirs, or lyo-jects. The container may be formed from a variety of materials such as glass or plastic. In some embodiments, a container is a pre-filled syringe. Suitable pre-filled syringes include, but are not limited to, borosilicate glass syringes with baked silicone coating, borosilicate glass syringes with sprayed silicone, or plastic resin syringes without silicone.

Typically, the container may hold formulations and a label on, or associated with, the container that may indicate directions for reconstitution and/or use. For example, the label may indicate that the formulation is reconstituted to concentrations as described above. The label may further indicate that the formulation is useful or intended for, for example, subcutaneous administration. In some embodiments, a container may contain a single dose of a stable formulation containing an angiotensin (1-7) peptide (e.g., a compound of SEQ ID NO:1) or a functional derivative thereof. In various embodiments, a single dose of the stable formulation is present in a volume of less than about 15 ml, 10 ml, 5.0 ml, 4.0 ml, 3.5 ml, 3.0 ml, 2.5 ml, 2.0 ml, 1.5 ml, 1.0 ml, or 0.5 ml. Alternatively, a container holding the formulation may be a multi-use vial, which allows for repeat administrations (e.g., from 2-6 administrations) of the formulation. Kits or other articles of manufacture may further include a second container comprising a suitable diluent (e.g., BWFI, saline, buffered saline). Upon mixing of the diluent and the formulation, the final protein concentration in the reconstituted formulation will generally be at least 1 mg/ml (e.g., at least 5 mg/ml, at least 10 mg/ml, at least 20 mg/ml, at least 30 mg/ml, at least 40 mg/ml, at least 50 mg/ml, at least 75 mg/ml, at least 100 mg/ml). Kits or other articles of manufacture may further include other materials desirable from a commercial and user standpoint, including other buffers, diluents, filters, needles, syringes, and package inserts with instructions for use. In some embodiments, kits or other articles of manufacture may include an instruction for self-administration.

EXAMPLES

This invention is further illustrated by the following examples, which should not be construed as limiting. Those skilled in the art will recognize, or be able to ascertain, using no more than routine experimentation, numerous equivalents to the specific substances and procedures described herein. Such equivalents are intended to be encompassed in the scope of the claims that follow the examples below.

Example 1—Administration of an Angiotensin(1-7) Peptide to Non-Ambulatory Subjects with Duchenne Muscular Dystrophy An angiotensin (1-7) peptide (e.g., a compound of SEQ ID NO:1) is administered to a non-ambulatory subject with Duchenne muscular dystrophy (DMD). For example, a patient has a left ventricle ejection fraction (EF) that is at or below 55%, e.g., an ejection fraction that is about 35% to about 55%). Patients can have stable cardiac function and can continue any pre-existing therapeutic regimens (e.g., patients can continue with any pre-existing cardiac medications).

An angiotensin (1-7) peptide (e.g., a compound of SEQ ID NO:1) is delivered via a subcutaneous injection to the patient. A subcutaneous injection is administered to a subject once daily at a dose that is about 1 mg/kg. A patient is administered subcutaneous injections of an angiotensin (1-7) peptide at this dose for about one year.

Therapeutic effects of an angiotensin (1-7) peptide (e.g., a compound of SEQ ID NO:1) are assessed using methods known in the art. For example, cardiac function is assessed using cardiac MRI and the measurement of EF with or without strain parameters. Myocardial fibrosis can also be measured using MRI (e.g., by late gadolinium enhancement cardiovascular magnetic resonance). Assessment of the therapeutic effect can occur periodically throughout treatment: for example, cardiac function is assessed prior to treatment, at about six months following initiation of treatment, and at about twelve months following initiation of treatment.

The invention claimed is:

1. A method of treating cardiac disease or disorder in a patient diagnosed with Duchenne muscular dystrophy (DMD) or Becker muscular dystrophy, the method comprising administering an angiotensin (1-7) peptide to a patient suffering from the cardiac disease or disorder and diagnosed with Duchenne muscular dystrophy (DMD) or Becker muscular dystrophy, wherein the angiotensin (1-7) peptide is administered once daily at a dose of 0.1 mg/kg to about 5.0 mg/kg, for a period of at least one to twenty-four months, and wherein the cardiac disease or disorder is selected from the group consisting of cardiomyopathy, cardiac arrhythmia, heart failure, left ventricular dysfunction, myocardial fibrosis (MF) and a conduction disorder.

2. The method of claim 1, wherein the patient is non-ambulatory.

3. The method of claim 1, wherein the cardiomyopathy is genetic.

4. The method of claim 3, wherein the genetic cardiomyopathy is hypertrophic cardiomyopathy (HCM), arrhymthogenic right ventricular cardiomyopathy/dysplasia (ARVC/D), conduction system diseases, LV non-compaction, an ion channelopathy, long-QT syndrome (LQTS), Brugada syndrome, catecholaminergic polymorphic ventricular tachycardia (CPVT), short-QT syndrome (SQTS) or idiopathic ventricular fibrillation.

5. The method of claim 1, wherein the angiotensin (1-7) peptide is the peptide of SEQ ID NO: 1.

6. The method of claim 1, wherein the angiotensin (1-7) peptide is a functional equivalent of SEQ ID NO:1.

7. The method of claim 1 wherein the patient is non-ambulatory and the administration of the angiotensin (1-7) peptide is subcutaneous.

8. The method of claim 7, wherein the angiotensin (1-7) peptide is the peptide of SEQ ID NO: 1.

9. The method of claim 7, wherein the angiotensin (1-7) peptide is a functional equivalent of SEQ ID NO: 1.

10. The method of claim 1, wherein the cardiac disease or disorder is cardiomyopathy.

11. The method of claim 10, wherein the cardiomyopathy is genetic.

12. The method of claim 11, wherein the genetic cardiomyopathy is hypertrophic cardiomyopathy (HCM), arrhymthogenic right ventricular cardiomyopathy/dysplasia (ARVC/D), conduction system diseases, LV non-compaction, an ion channelopathy, long-QT syndrome (LQTS), Brugada syndrome, catecholaminergic polymorphic ventricular tachycardia (CPVT), short-QT syndrome (SQTS) or idiopathic ventricular fibrillation.

13. The method of claim 7, wherein the cardiac disease or disorder is cardiac arrhythmia.

14. The method of claim 1 wherein the angiotensin (1-7) peptide is administered for a period greater than twenty-four months.

15. The method of claim 1, wherein the administering an angiotensin (1-7) peptide to the patient is oral.

16. The method of claim 1, wherein the method comprises treating cardiac disease or disorder in a patient diagnosed with Duchenne muscular dystrophy (DMD).

17. The method of claim 1, wherein the method comprises treating cardiac disease or disorder in a patient diagnosed with Becker muscular dystrophy (BMD).

18. The method of claim 1, wherein the angiotensin (1-7) peptide is administered at a dose of about 0.5 mg/kg to about 2.0 mg/kg.

19. The method of claim 1, wherein the angiotensin (1-7) peptide is administered at a dose of about 0.5 mg/kg.

* * * * *

SEQUENCE LISTING

```
<160> NUMBER OF SEQ ID NOS: 6

<210> SEQ ID NO 1
<211> LENGTH: 7
<212> TYPE: PRT
<213> ORGANISM: Unknown
<220> FEATURE:
<223> OTHER INFORMATION: Description of Unknown:
      Angiotensin (1-7) sequence

<400> SEQUENCE: 1

Asp Arg Val Tyr Ile His Pro
1               5

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Asp Arg Val Ser Ile His Cys
1               5

<210> SEQ ID NO 3
<211> LENGTH: 12
<212> TYPE: PRT
<213> ORGANISM: Unknown
<220> FEATURE:
<223> OTHER INFORMATION: Description of Unknown:
      Angiotensinogen sequence

<400> SEQUENCE: 3

Asp Arg Val Tyr Ile His Pro Phe His Leu Val Ile
1               5                   10

<210> SEQ ID NO 4
<211> LENGTH: 7
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid or absent
<220> FEATURE:
<221> NAME/KEY: MOD_RES
<222> LOCATION: (2)..(2)
<223> OTHER INFORMATION: Arg, Lys, Ala, Cit (citrulline), Orn
      (ornithine), acetylated Ser, Sar, D-Arg and D-Lys
<220> FEATURE:
<221> NAME/KEY: MOD_RES
<222> LOCATION: (3)..(3)
<223> OTHER INFORMATION: Val, Ala, Leu, Nle (norleucine), Ile, Gly, Lys,
      Pro, HydroxyPro (hydroxyproline), Aib (2-aminoisobutyric acid),
      Acpc (1-aminocyclopentane carboxylic acid) or Tyr
<220> FEATURE:
<221> NAME/KEY: MOD_RES
<222> LOCATION: (4)..(4)
<223> OTHER INFORMATION: Tyr, Tyr(PO3), Thr, Ser, homoSer (homoserine),
      azaTyr (aza-alpha1-homo-L-tyrosine) or Ala
<220> FEATURE:
<221> NAME/KEY: MOD_RES
<222> LOCATION: (5)..(5)
<223> OTHER INFORMATION: Ile, Ala, Leu, norLeu, Val or Gly
<220> FEATURE:
<221> NAME/KEY: MOD_RES
<222> LOCATION: (6)..(6)
<223> OTHER INFORMATION: His, Arg or 6-NH2-Phe (6-aminophenylalanine)
<220> FEATURE:
<221> NAME/KEY: MOD_RES
<222> LOCATION: (7)..(7)
<223> OTHER INFORMATION: Cys, Pro or Ala
<220> FEATURE:
<223> OTHER INFORMATION: See specification as filed for detailed
      description of substitutions and preferred embodiments

<400> SEQUENCE: 4

Xaa Xaa Xaa Xaa Xaa Xaa Xaa
1               5

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Norleucine

<400> SEQUENCE: 5

Asp Arg Leu Tyr Ile His Pro
1               5

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Asp Arg Val Ser Ile His Cys
1               5
```